United States Patent [19]

Budt et al.

[11] Patent Number: 5,804,559
[45] Date of Patent: Sep. 8, 1998

[54] PRODRUG DERIVATIVES OF ENZYME INHIBITORS HAVING HYDROXYL GROUPS, A PROCESS FOR PREPARING THEM, AND THEIR USE

[75] Inventors: Karl-Heinz Budt, Kelkheim; Bernd Stowasser, Rüsselsheim; Anuschirwan Peyman, Kelkheim; Jochen Knolle, Kriftel; Irvin Winkler, Liederbach; Hans Gerd Berscheid, Kronberg, all of Germany

[73] Assignee: Hoechst Aktiengesellschaft, Frankfurt am Main, Germany

[21] Appl. No.: 525,525

[22] PCT Filed: Feb. 25, 1994

[86] PCT No.: PCT/EP94/00561

§ 371 Date: Sep. 12, 1995

§ 102(e) Date: Sep. 12, 1995

[87] PCT Pub. No.: WO94/21604

PCT Pub. Date: Sep. 29, 1994

[30] Foreign Application Priority Data

Mar. 13, 1993 [DE] Germany .......................... 43 08 096.0

[51] Int. Cl.$^6$ ............................. A61K 38/00; C07K 5/00
[52] U.S. Cl. ............................. 514/17; 514/18; 514/19; 530/323; 530/330; 530/331
[58] Field of Search .................... 530/330, 331, 530/323; 514/17, 18, 19

[56] References Cited

FOREIGN PATENT DOCUMENTS

| 2026382 | 3/1991 | Canada . |
| 0 428 849 A2 | 5/1991 | European Pat. Off. . |
| WO 92/16501 | 10/1992 | WIPO . |

OTHER PUBLICATIONS

Bolis et al. J. Med. Chem. 30(10) pp. 1729–1737 (1987).
Bundgaard *Design of Prodrugs* CH. 1 (1985) pp. 1–24.
Silverman, The Organic Chemistry of Drug Design and Drug Action (Academic Press, Inc. 1992) pp. 352–401.
Aggarwal et al., J. Med. Chem. vol. 33 (1990) 1505–1510.

*Primary Examiner*—Cecilia J. Tsang
*Assistant Examiner*—Bennett Celsa
*Attorney, Agent, or Firm*—Finnegan, Henderson, Farabow, Garrett & Dunner, L.L.P.

[57] ABSTRACT

The invention concerns prodrugs of enzyme inhibitors in which at least one OH— group in the enzyme inhibitor has been converted into a derivative grouping of the formula III, IV or V:

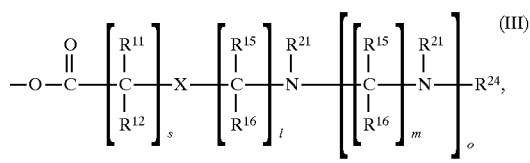

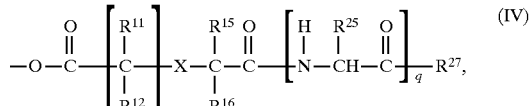

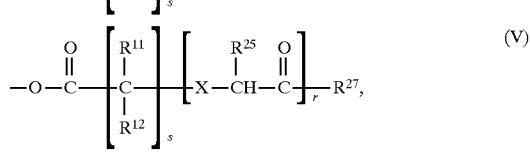

in which the groups $R^{11}$ to $R^{25}$ and s, l, m, o, q, and r are as defined in the description. Such prodrugs exhibit an improved solubility in water and improved pharmacokinetic characteristics.

6 Claims, 3 Drawing Sheets

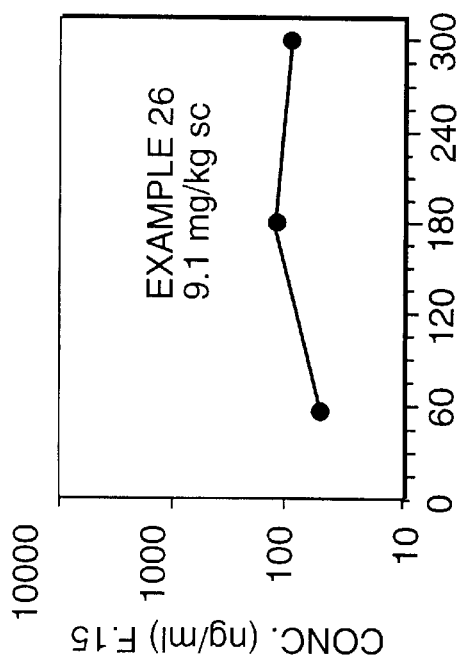
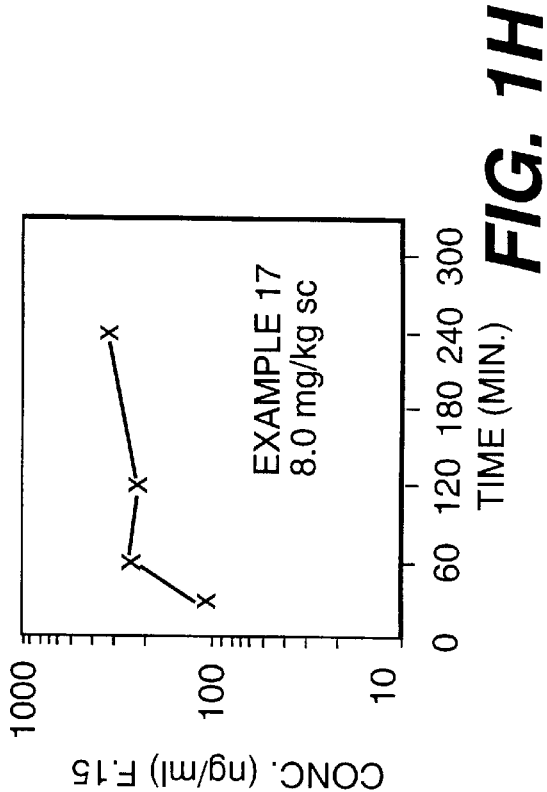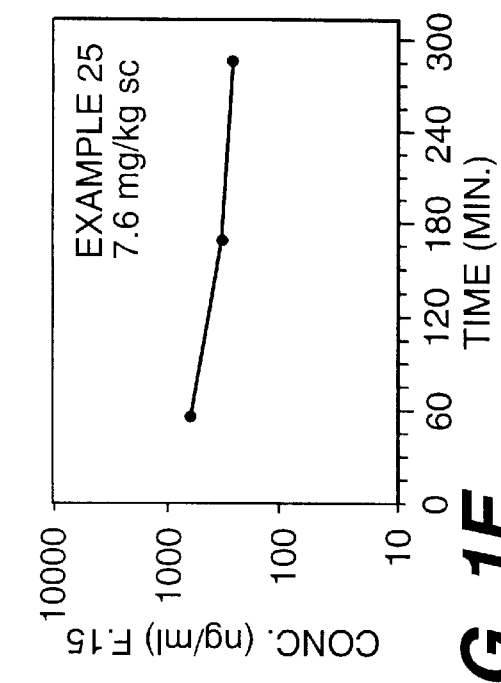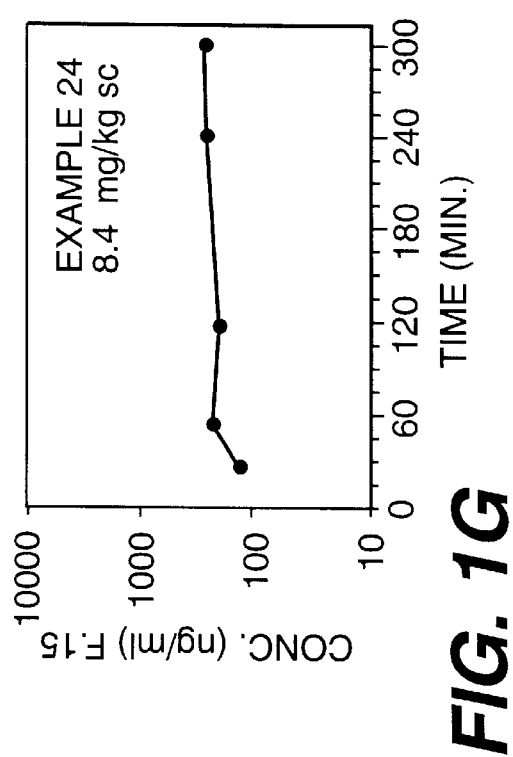

PRODRUG DERIVATIVES OF ENZYME INHIBITORS HAVING HYDROXYL GROUPS, A PROCESS FOR PREPARING THEM, AND THEIR USE

This application is a 371 of PCT/EP94/00561 filed Feb. 25, 1994.

FIELD OF THE INVENTION

The present invention relates to prodrugs with the aid of which the water-solubility and pharmaco kinetic parameters of enzyme inhibitors can be improved.

DESCRIPTION OF THE PRIOR ART

It is known that a wide diversity of compounds having a hydroxyl group (—OH) are beneficial active compounds for treatment of or combating various clinical syndromes or states. It is also known that such compounds corresponding to the prior art sometimes have a certain intrinsic disadvantage, in particular problems with bioavailability after administration and problems with the stability or the pharmaceutical formulation. Such a reduced bio-availability can sometimes be attributed to poor solubility in water and also to metabolism losses during and after conventional administration. The poor water-solubility of many products corresponding to the prior art also makes it difficult or impossible to prepare formulations which are suitable for intravenous or intramuscular injections or ophthalmic uses.

A promising approach to solving these problems lay in esterification of the hydroxyl function of active compounds in order to obtain pharmacologically improved prodrug forms.

Some types of esters have already been described as prodrugs of hydroxyl-containing active compounds (Hans Bundgaard, Design of Prodrugs, Elsevier Science Publishers B. V., Amsterdam, 1985).

These ester prodrugs are dependent on enzymatic hydrolysis (esterases) in order to obtain usable conversion rates of prodrugs into active compounds. This approach accordingly has several disadvantages:

1) There are wide variations in esterase concentrations in various individuals. This can lead to nonuniform and unpredictable levels of active compound.
2) The rate of enzymatic hydrolysis of the esters by esterases depends both on the acid and also on the hydroxyl-containing part of the ester (Bundgaard, loc. cit.). Some esters, for example esters of sterically demanding hydroxyl-containing active compounds, are very poor substrates for esterases.

SUMMARY OF THE INVENTION

It is the aim of this invention to provide ester prodrugs of hydroxyl-containing medicaments in which the above-mentioned disadvantages do not occur.

DESCRIPTION OF THE PREFERRED EMBODIMENTS

It has now been found that certain prodrugs of enzyme inhibitors do not have the abovementioned disadvantages. The invention accordingly relates to compounds of the formula I in which radicals which occur several times and are defined in the same way can be independent of one another $$W\text{-}[R^5]_a \qquad \qquad I$$

in which W is a mono-, bis- or tris-dehydroxylated radical of an enzyme inhibitor, a is 1, 2 or 3 and $R^5$ is a radical of the formula III, IV or V

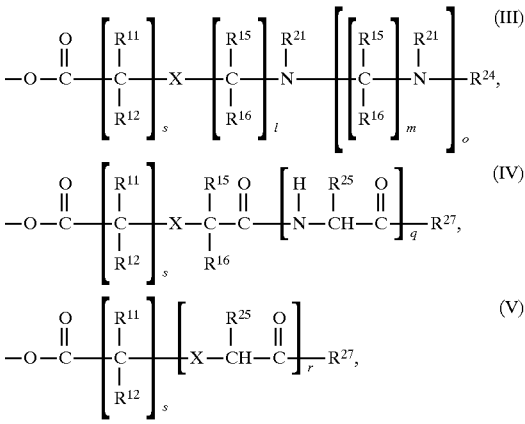

$R^5$ is preferably a radical of the formula III or IV, and $R^5$ is particularly preferably a radical of the formula III, X is O, S, $NR^{20}$ or $N^+(R^{20})_2$, preferably S or $NR^{20}$, in which $R^{20}$ is H, $(C_1–C_6)$-alkyl, $(C_3–C_7)$-cycloalkyl, $—CH_2—(CH_2)_n—NR^{21}R^{24}$, $—CH_2—C(O)—R^{28}CH_2CONH(C_1–C_6)$-alkyl, which can be substituted by up to 5 OH groups, $COO(C_1–C_6)$-alkyl or $—CH_2—P(O)((C_1–C_4)\text{-alkyl})_2$, preferably H, $(C_1–C_4)$-alkyl, or $—CH_2—C(O)—R^{28}$ or $—CH_2—P(O)Me_2$, particularly preferably H or $(C_1–C_4)$-alkyl, $R^{11}$, $R^{12}$, $R^{15}$ and $R^{16}$ independently of one another are H or $(C_1–C_4)$-alkyl, preferably H or methyl, $R^{21}$ is H, $(C_1–C_6)$-alkyl, $(C_3–C_7)$-cycloalkyl or $(C_1–C_4)$-alkyloxycarbonyl, preferably H or $(C_1–C_4)$-alkyl, $R^{24}$ is H, $(C_1–C_{18})$-alkyl, $(C_3–C_{14})$-cycloalkyl, $(C_2–C_{18})$-alkenyl, $(C_2–C_{18})$-alkynyl or $(C_6–C_{14})$-aryl, each of which can be mono-, di- or trisubstituted by $(C_6–C_{14})$-aryl, $(C_6–C_{14})$-aryloxy, $(C_3–C_{14})$-cycloalkyl, hydroxyl, $(C_1–C_4)$-alkoxy, $—C(O)—R^{28}$, $P(O)((C_1–C_4)\text{-alkyl})_2$, $NH_2$ or halogen and are linked with $NR^{21}$ directly or optionally via CO, or an α-amino acid linked via the carbonyl group, or $R^{24}$ is $((C_1–C_4)\text{-alkyl})$ $-N((C_1–C_4)\text{-alkyl})$-$(C_1–C_4)$-alkyl-NH—$((C_1–C_4)$-alkyl), or $R^{24}$ forms a heterocyclic radical with $R^{21}$, and $R^{24}$ is preferably H, $(C_1–C_4)$-alkyl, which can optionally be substituted by phenyl, $NH_2$ or $(C_3–C_7)$-cycloalkyl and is linked with $NR^{21}$ directly or optionally via CO, a naturally occurring α-amino acid linked via the carbonyl group, $—CH_2C(O)R^{28}$, $—C_2—P(O)Me_2$ or $—(CH_2)_3N(Me)(CH_2)_2NHMe$, and $R^{24}$ is particularly preferably H or $(C_1–C_4)$-alkyl, $R^{25}$ is a side chain of an amino acid, preferably a side chain of Asp, Glu, Lys, Arg or Orn, $R^{27}$ and $R^{28}$ independently of one another are OH, O—$(C_1–C_6)$-alkyl, O—$(C_3–C_7)$-cycloalkyl, $NH_2$, —NH—$(C_1–C_6)$-alkyl, which can be substituted by up to 5 OH groups, —NH—$(C_3–C_7)$-cycloalkyl or —N-bis$(C_1–C_4)$-alkyl, $R^{27}$ and $R^{28}$ are preferably independently of one another OH, $NH_2$, O$(C_1–C_4)$-alkyl, —NH—$(C_1–C_4)$-alkyl or —N-bis$(C_1–C_4)$-alkyl, and $R^{27}$ and $R^{28}$ are particularly preferably independently of one another OH, $NH_2$ or O$(C_1–C_4)$-alkyl, in which l can be 2 or 3, preferably 2, s can be 1, 2, 3, 4 or 5, preferably 1, 4 or 5, particularly preferably 1, m can be 0, 1, 2, 3 or 4, preferably 2 or 3, n can be 1, 2 or 3, preferably 1 or 2, o can be 0, 1, 2 or 3, preferably 0, 1 or 2, particularly preferably 0, q can be 0, 1, 2 or 3, preferably 1 or 2, particularly preferably 1, and r can be 1, 2 or 3, preferably 1 or 2.

Preferred enzyme inhibitors are protease inhibitors, inhibitors of retroviral proteases are particularly preferred, and inhibitors of HIV protease may be mentioned as examples.

The following protease inhibitors are furthermore particularly preferred, the formulae in question being interpreted as the mono-, bis- or tris-dehydroxylated radicals W— in respect of the compounds W—(R$^5$)a according to the invention.

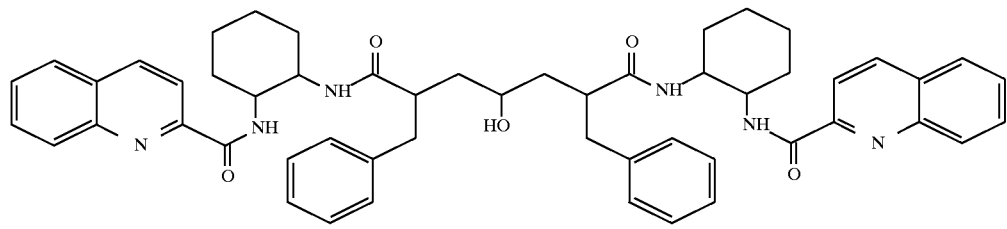

F.1

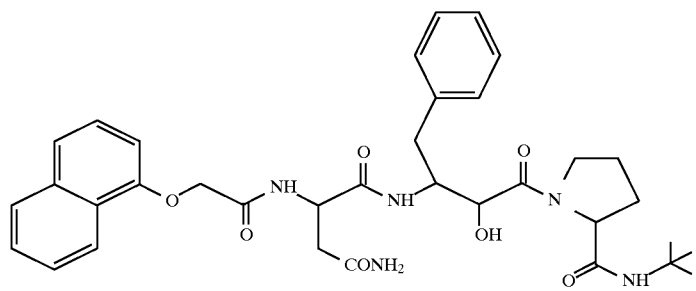

J. Med. Chem., 35, 1319, (1992)

F.2

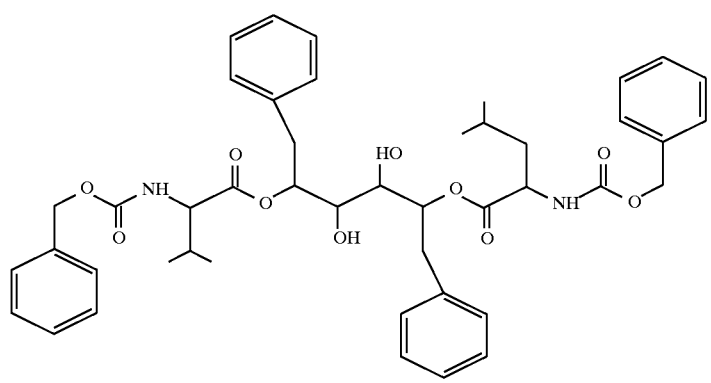

WO 92 16501-A

F.3

-continued
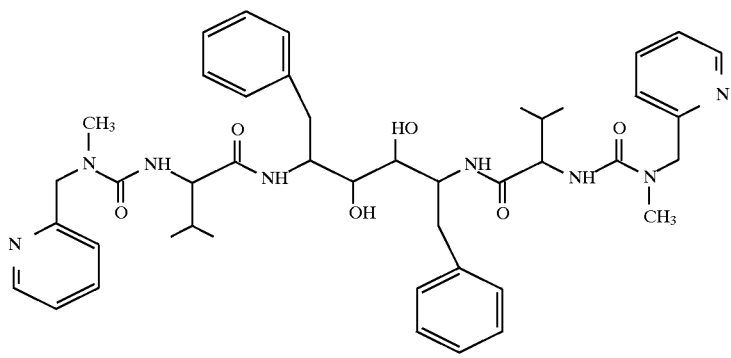
Antimicrobial Agents and Chemotherapy, 35, 2209, (1991)
F.4
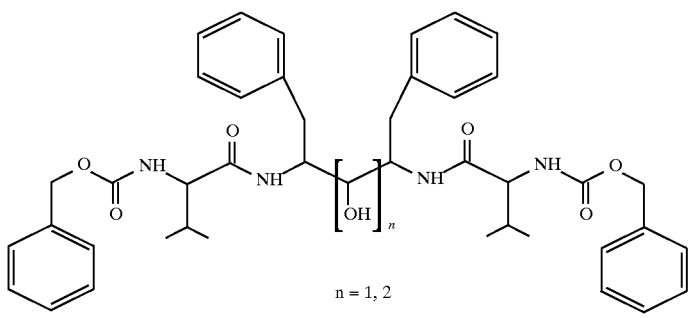
n = 1, 2
J. Med. Chem., 35, 2687, (1990)
Antimicrobial Agents and Chemotherapy, 35, 2209, (1991)
F.5
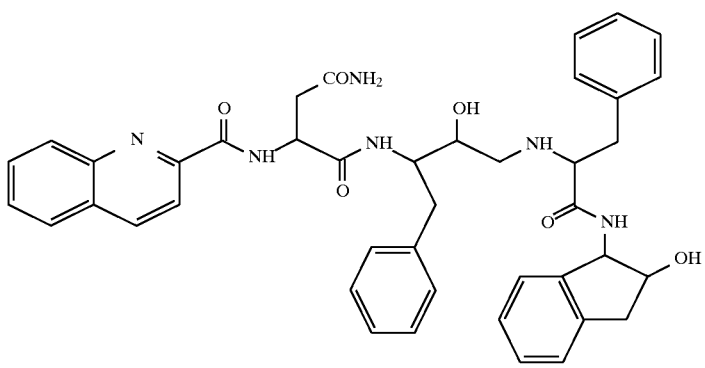
J. Med. Chem., 35, 2528, (1992)
F.6
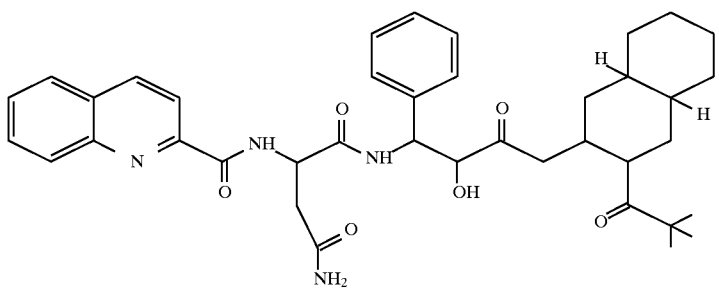
F.7

-continued
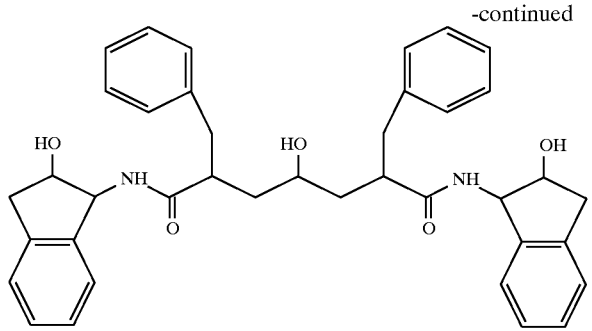
J. Med. Chem., 34, 9382, (1991)
F.8
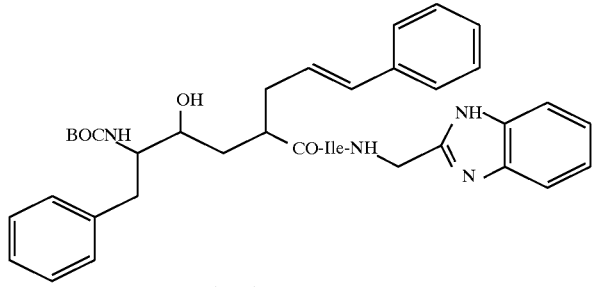
J. Med. Chem., 34, 1226, (1991)
F.9
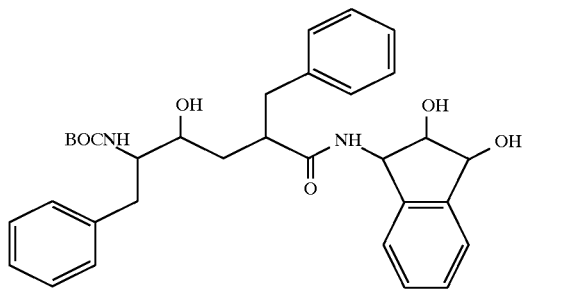
J. Med. Chem., 34, 1228, (1991)
F.10
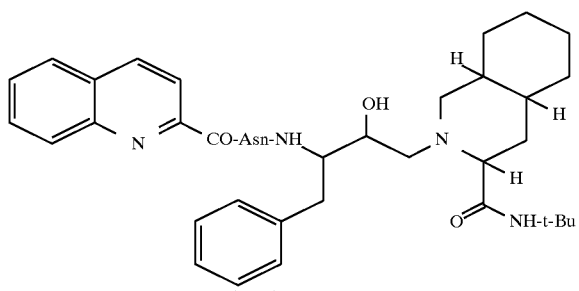
Antiviral Research, 17, 265, (1992)
F.11
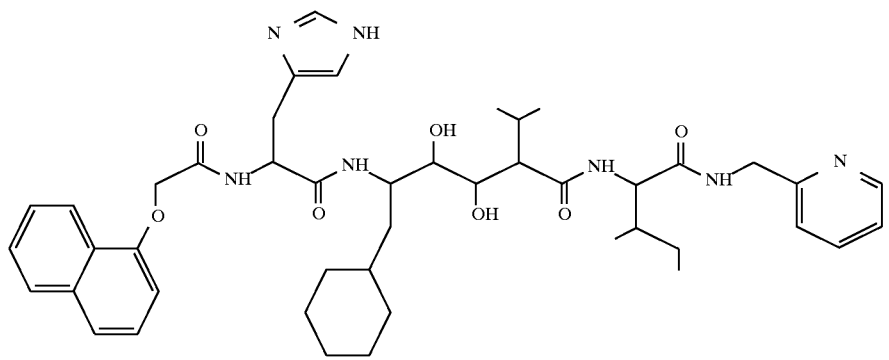
J. Med. Chem., 34, 2348, (1991)
F.12

F.13
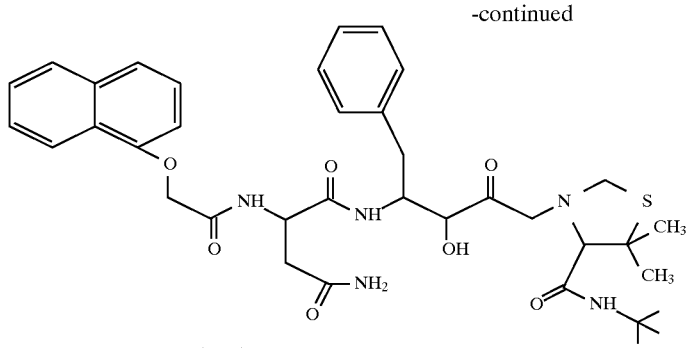
Peptide Chemistry, 399, (1991)
F.14
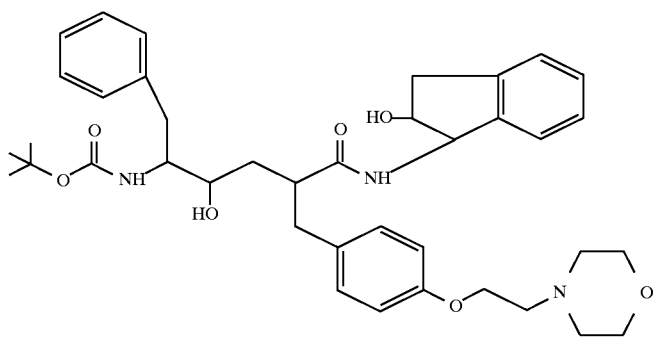
Biochem. Biophys. Res. Commun., 181, 1459, (1991)
F.15
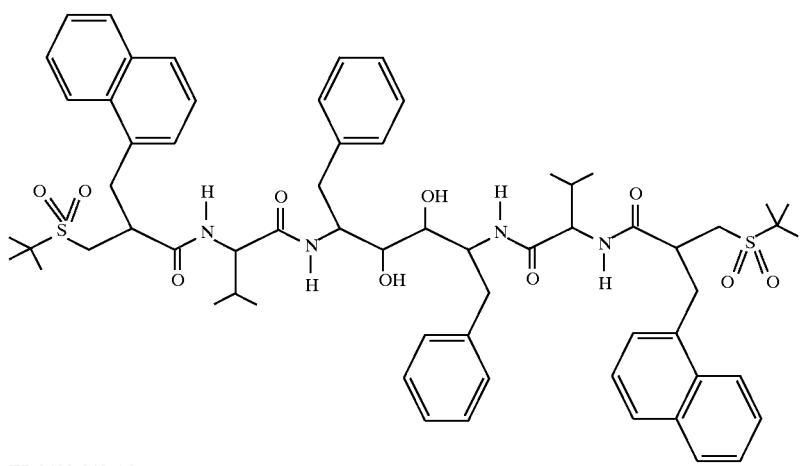
EP 0428 849 A2
F.16
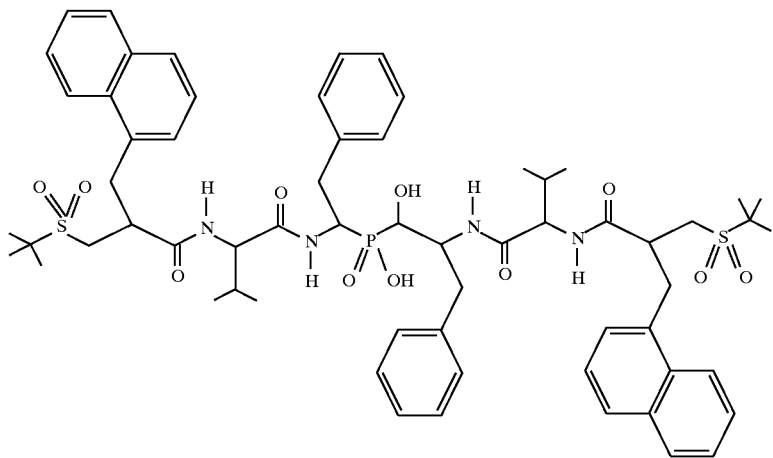
P 42 20566.2

-continued

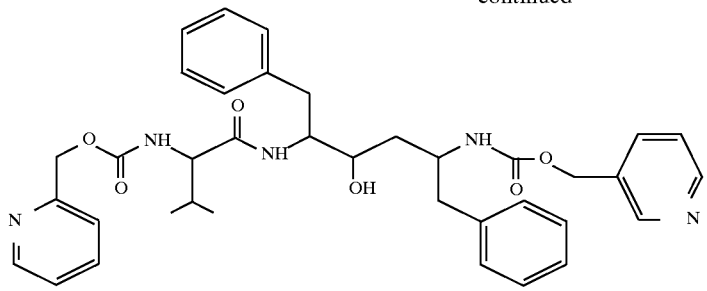

F.17

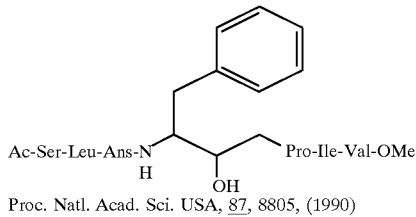

F.18

Ac-Ser-Leu-Ans-N(H)—...—Pro-Ile-Val-OMe

Proc. Natl. Acad. Sci. USA, 87, 8805, (1990)

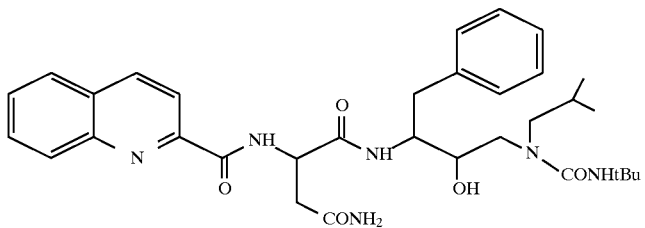

F.19

Particularly preferred compounds according to the invention are compounds of the formula I'

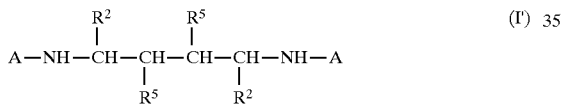

in which A is a radical D-G, in which
G is an amino acid, preferably a naturally occurring amino acid or an amino acid from the series consisting of Val, Nva (norvaline), Ile, Ala, Tbg (tert-butylglycine), Chg (cyclohexylglycine), Cpg (cyclopentylglycine), Glu, Asn and Gln and
D is a radical of the formula II

in which
$R^1$ is chosen from the group consisting of phenylsulfonyl which is optionally substituted by halogen, methoxy or $(C_1-C_4)$-alkyl; benzylsulfonyl which is optionally substituted by halogen, methoxy or $(C_1-C_4)$-alkyl; $(C_1-C_{12})$-alkylsulfonyl which is optionally substituted by up to three radicals independent of one another chosen from the group consisting of hydroxyl, amino and carboxyl; Het-sulfonyl; and Het-$(C_1-C_6)$-alkylsulfonyl; in which Het is pyrrolyl, imidazolyl, pyridyl, pyrimidyl, quinolyl or isoquinolyl, which can optionally be substituted by up to two substituents independent of one another chosen from the group consisting of $(C_1-C_4)$-alkyl, hydroxyl and amino; $R^1$ is preferably phenylsulfonyl or benzylsulfonyl, in each case optionally substituted by chlorine, methoxy or methyl; or $(C_1-C_{12})$-alkylsulfonyl which is optionally substituted by hydroxyl; $R^1$ is particularly preferably $(C_1-C_6)$-alkylsulfonyl, $R^2$ is chosen from the group consisting of hydrogen, carboxyl, methyl, ethyl, isopropyl, n-propyl, n-butyl, isobutyl, sec-butyl, pentyl, hexyl, cyclohexyl, cyclopentylmethyl, cyclohexylmethyl, cycloheptylmethyl, 4-methylcyclohexylmethyl, 1-decahydronaphthylmethyl, 2-decahydronaphthylmethyl, phenyl, benzyl, 2-phenylethyl, 1-naphthylmethyl, 2-naphthylmethyl, 2-methylbenzyl, 3-methylbenzyl, 4-methylbenzyl, 2,4,6-trimethylbenzyl, 4-tert-butylbenzyl, 4-tert-butoxybenzyl, 4-hydroxybenzyl, 4-methoxybenzyl, 2,4-dimethoxybenzyl, 3,4-dihydroxybenzyl, 3,4-dimethoxybenzyl, (benzodioxolan-4-yl)methyl, 4-chlorobenzyl, hydroxymethyl, 1-hydroxyethyl, 2-pyridylmethyl, 3-pyridylmethyl, 4-pyridylmethyl, 2-(4-pyridyl)ethyl, 2-thienylmethyl, 3-thienylmethyl, 2-(2-thienyl)ethyl, 2-(3-thienyl)ethyl, indol-2-ylmethyl, indol-3-ylmethyl, (1-methylimidazol-4-yl)methyl, imidazol-4-ylmethyl, imidazol-1-ylmethyl, 2-thiazolylmethyl, 3-pyrazolylmethyl, 4-pyrimidylmethyl, 2-benzo[b]thienylmethyl, 3-benzo[b]thienylmethyl, 2-furylmethyl, 2-(methylthio)ethyl, 2-(methylsulfinyl)ethyl and 2-(methylsulfonyl)ethyl; $R^2$ is preferably hydrogen, methyl, ethyl, isopropyl, n-propyl, n-butyl, isobutyl, sec-butyl, n-pentyl, n-hexyl, cyclopentylmethyl, cyclohexylmethyl, cycloheptylmethyl, 4-methylcyclohexylmethyl, benzyl, 2-phenylethyl, 1-naphthylmethyl, 2-naphthylmethyl, 2-methylbenzyl, 3-methylbenzyl, 4-methylbenzyl, 2,4,6-trimethylbenzyl, 4-tert-butylbenzyl, 4-hydroxybenzyl, 4-methoxybenzyl, 2,4-dimethoxybenzyl, 3,4-dimethoxybenzyl, 3,4-methylenedioxybenzyl, 4-chlorobenzyl and 2-(4-pyridyl)ethyl; $R^2$ is particularly preferably hydrogen, methyl, ethyl, isopropyl, n-propyl, n-butyl, isobutyl, sec-butyl, n-pentyl, n-hexyl, cyclohexylmethyl, benzyl, 2-phenylethyl, 4-methylbenzyl or 4-methoxybenzyl, $R^9$ is chosen from the group as defined for $R^2$ and tert-butylsulfonylmethyl; $R^9$ is preferably hydrogen, methyl, ethyl, isopropyl, n-propyl, n-butyl, isobutyl, sec-butyl, n-pentyl, n-hexyl, cyclopentylmethyl, cyclohexylmethyl, cycloheptylmethyl, 4-methylcyclohexylmethyl, 1-decahydronaphthylmethyl, 2-decahydronaphthylmethyl, benzyl, 2-phenylethyl, 1-naphthylmethyl, 2-naphthylmethyl, 2-methylbenzyl, 3-methylbenzyl, 4-methylbenzyl, 2,4,6-trimethylbenzyl, 4-methoxybenzyl, 4-chlorobenzyl, 4-pyridylmethyl, 2-thienylmethyl, 3-thienylmethyl or tert-butylsulfonylmethyl;

$R^9$ is particularly preferably hydrogen, methyl, ethyl, isopropyl, n-propyl, n-butyl, isobutyl, secbutyl, n-pentyl, n-hexyl, cyclopentylmethyl, cyclohexylmethyl, benzyl, 2-phenylethyl, 1-naphthyl5 methyl, 2-naphthylmethyl, 4-methylbenzyl, 2,4,6-trimethylbenzyl, 4-methoxybenzyl or 4-chlorobenzyl, and $R^5$ is as defined above, and $R^{5*}$ can have the meanings mentioned above for $R^5$, independently of $R^5$, or can be hydrogen or hydroxyl.

Particularly preferred radicals $R^5$ with which the OH groups of the abovementioned compounds are derivatized are the following radicals:

|  | $R^{30}$ | $R^{31}$ | $R^{32}$ |
|---|---|---|---|
| I.1.1 | H | H | H |
| I.1.2 | methyl | H | H |
| I.1.3 | ethyl | H | H |
| I.1.4 | H | methyl | H |
| I.1.5 | H | ethyl | H |
| I.1.6 | H | propyl | H |
| I.1.7 | H | isopropyl | H |
| I.1.8 | H | butyl | H |
| I.1.9 | H | 2-butyl | H |
| I.1.10 | H | t-butyl | H |
| I.1.11 | H | cyclohexylmethyl | H |
| I.1.12 | H | 2-cyclohexylethyl | H |
| I.1.13 | H | benzyl | H |
| I.1.14 | methyl | methyl | H |
| I.1.15 | ethyl | ethyl | H |
| I.1.16 | propyl | propyl | H |
| I.1.17 | butyl | butyl | H |
| I.1.18 | methyl | ethyl | H |
| I.1.19 | methyl | propyl | H |
| I.1.20 | methyl | isopropyl | H |
| I.1.21 | methyl | butyl | H |
| I.1.22 | methyl | 2-butyl | H |
| I.1.23 | methyl | t-butyl | H |
| I.1.24 | methyl | cyclohexylmethyl | H |
| I.1.25 | methyl | 2-cyclohexylethyl | H |
| I.1.26 | methyl | benzyl | H |
| I.1.27 | H | methyl | methyl |
| I.1.28 | H | ethyl | ethyl |
| I.1.29 | methyl | methyl | methyl |
| I.1.30 | ethyl | ethyl | H |
| I.1.31 | methyl | —(CH$_2$)$_3$N(Me)CH$_2$CH$_2$NHMe | methyl |
| I.1.32 | —CH$_2$POMe$_2$ | methyl | H |
| I.1.33 | methyl | —CH$_2$POMe$_2$ | H |
| I.1.34 | —CH$_2$CO$_2$tBu | methyl | H |
| I.1.35 | —CH$_2$CO$_2$H | methyl | H |
| I.1.36 | —CH$_2$CO$_2$tBu | H | H |
| I.1.37 | —CH$_2$CO$_2$H | H | H |
| I.1.38 | methyl | —CH$_2$CO$_2$tBu | H |
| I.1.39 | methyl | —CH$_2$CO$_2$H | H |
| I.1.40 | H | —CH$_2$CO$_2$tBu | H |
| I.1.41 | H | —CH$_2$CO$_2$H | H |
| I.1.42 | methyl | glycyl | methyl |
| I.1.43 | methyl | glycyl | H |
| I.1.44 | H | glycyl | H |
| I.1.45 | H | glycyl | methyl |
| I.1.46 | methyl | arginyl | methyl |
| I.1.47 | methyl | arginyl | H |
| I.1.48 | H | arginyl | H |
| I.1.49 | H | arginyl | methyl |
| I.1.50 | methyl | glutamyl | methyl |
| I.1.51 | methyl | glutamyl | H |
| I.1.52 | H | glutamyl | H |
| I.1.53 | H | glutamyl | methyl |
| I.1.54 | methyl | lysyl | methyl |
| I.1.55 | methyl | lysyl | H |
| I.1.56 | H | lysyl | H |
| I.1.57 | H | lysyl | methyl |
| I.1.58 | methyl | asparagyl | methyl |
| I.1.59 | methyl | asparagyl | H |
| I.1.60 | H | asparagyl | H |
| I.1.61 | H | asparagyl | methyl |
| I.1.62 | methyl | sarcosyl | methyl |
| I.1.63 | methyl | sarcosyl | H |
| I.1.64 | H | sarcosyl | H |
| I.1.65 | H | sarcosyl | methyl |
| I.1.66 | methyl | acetyl | H |
| I.1.67 | H | acetyl | H |
| I.1.68 | methyl | propionyl | H |
| I.1.69 | H | propionyl | H |
| I.1.70 | methyl | butanoyl | H |
| I.1.71 | H | butanoyl | H |
| I.1.72 | methyl | pivaloyl | H |
| I.1.73 | H | pivaloyl | H |
| I.1.74 | methyl | pentanoyl | H |
| I.1.75 | H | pentanoyl | H |
| I.1.76 | methyl | hexanoyl | H |
| I.1.77 | H | hexanoyl | H |
| I.1.78 | methyl | benzoyl | H |
| I.1.79 | H | benzoyl | H |
| I.1.80 | methyl | phenylacetyl | H |
| I.1.81 | H | phenylacetyl | H |
| I.1.82 | methyl | 3-phenylpropionyl | H |
| I.1.83 | H | 3-phenylpropionyl | H |
| I.1.84 | methyl | 3,3-dimethylbutanoyl | H |
| I.1.85 | H | 3,3-dimethylbutanoyl | H |

|  | $R^{30}$ | $R^{31}$ | $R^{32}$ |
|---|---|---|---|
| I.2.1 | H | 2-(methylamino)ethyl | methyl |
| I.2.2 | H | 2-(dimethylamino)ethyl | methyl |
| I.2.3 | H | —(CH$_2$)$_2$N(Me)(CH$_2$)$_3$NH$_2$ | methyl |
| I.2.4 | H | H | H |
| I.2.5 | methyl | H | H |
| I.2.6 | ethyl | H | H |
| I.2.7 | H | methyl | H |
| I.2.8 | H | ethyl | H |
| I.2.9 | H | propyl | H |
| I.2.10 | H | isopropyl | H |
| I.2.11 | H | butyl | H |
| I.2.12 | H | 2-butyl | H |
| I.2.13 | H | t-butyl | H |
| I.2.14 | H | cyclohexylmethyl | H |
| I.2.15 | H | 2-cyclohexylethyl | H |
| I.2.16 | H | benzyl | H |
| I.2.17 | methyl | methyl | H |
| I.2.18 | ethyl | ethyl | H |
| I.2.19 | propyl | propyl | H |
| I.2.20 | butyl | butyl | H |
| I.2.21 | methyl | ethyl | H |
| I.2.22 | methyl | propyl | H |
| I.2.23 | methyl | isopropyl | H |
| I.2.24 | methyl | butyl | H |
| I.2.25 | methyl | 2-butyl | H |
| I.2.26 | methyl | t-butyl | H |
| I.2.27 | methyl | cyclohexylmethyl | H |
| I.2.28 | methyl | 2-cyclohexylethyl | H |

| | | | |
|---|---|---|---|
| I.2.29 | methyl | benzyl | H |
| I.2.30 | H | methyl | methyl |
| I.2.31 | H | ethyl | ethyl |
| I.2.32 | methyl | methyl | methyl |
| I.2.33 | ethyl | ethyl | ethyl |
| I.2.34 | —CH$_2$CO$_2$tBu | methyl | H |
| I.2.35 | —CH$_2$CO$_2$H | methyl | H |
| I.2.36 | —CH$_2$CO$_2$tBu | H | H |
| I.2.37 | —CH$_2$CO$_2$H | H | H |
| I.2.38 | Me | —CH$_2$CO$_2$tBu | H |
| I.2.39 | Me | —CH$_2$CO$_2$H | H |
| I.2.40 | H | —CH$_2$CO$_2$tBu | H |
| I.2.41 | H | —CH$_2$CO$_2$H | H |
| I.2.42 | methyl | glycyl | methyl |
| I.2.43 | methyl | glycyl | H |
| I.2.44 | H | glycyl | H |
| I.2.45 | H | glycyl | methyl |
| I.2.46 | methyl | arginyl | methyl |
| I.2.47 | methyl | arginyl | H |
| I.2.48 | H | arginyl | H |
| I.2.49 | H | arginyl | methyl |
| I.2.50 | methyl | glutamyl | methyl |
| I.2.51 | methyl | glutamyl | H |
| I.2.52 | H | glutamyl | H |
| I.2.53 | H | glutamyl | methyl |
| I.2.54 | methyl | lysyl | methyl |
| I.2.55 | methyl | lysyl | H |
| I.2.56 | H | lysyl | H |
| I.2.57 | H | lysyl | methyl |
| I.2.58 | methyl | asparagyl | methyl |
| I.2.59 | methyl | asparagyl | H |
| I.2.60 | H | asparagyl | H |
| I.2.61 | H | asparagyl | methyl |
| I.2.62 | methyl | sarcosyl | methyl |
| I.2.63 | methyl | sarcosyl | H |
| I.2.64 | H | sarcosyl | H |
| I.2.65 | H | sarcosyl | methyl |
| I.2.66 | methyl | acetyl | H |
| I.2.67 | H | acetyl | H |
| I.2.68 | methyl | propionyl | H |
| I.2.69 | H | propionyl | H |
| I.2.70 | methyl | butanoyl | H |
| I.2.71 | H | butanoyl | H |
| I.2.72 | methyl | pivaloyl | H |
| I.2.73 | H | pivaloyl | H |
| I.2.74 | methyl | pentanoyl | H |
| I.2.75 | H | pentanoyl | H |
| I.2.76 | methyl | hexanoyl | H |
| I.2.77 | H | hexanoyl | H |
| I.2.78 | methyl | benzoyl | H |
| I.2.79 | H | benzoyl | H |
| I.2.80 | methyl | phenylacetyl | H |
| I.2.81 | H | phenylacetyl | H |
| I.2.82 | methyl | 3-phenylpropionyl | H |
| I.2.83 | H | 3-phenylpropionyl | H |
| I.2.84 | methyl | 3,3-dimethylbutanoyl | H |
| I.2.85 | H | 3,3-dimethylbutanoyl | H |

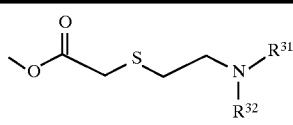

I.3.

| | R$^{31}$ | R$^{32}$ |
|---|---|---|
| I.3.1 | H | H |
| I.3.2 | methyl | H |
| I.3.3 | ethyl | H |
| I.3.4 | propyl | H |
| I.3.5 | isopropyl | H |
| I.3.6 | butyl | H |
| I.3.7 | 2-butyl | H |
| I.3.8 | t-butyl | H |
| I.3.9 | cyclohexylmethyl | H |
| I.3.10 | 2-cyclohexylethyl | H |
| I.3.11 | benzyl | H |
| I.3.12 | methyl | methyl |
| I.3.13 | ethyl | ethyl |
| I.3.14 | —CH$_2$CO$_2$tBu | H |
| I.3.15 | —CH$_2$CO$_2$H | H |
| I.3.16 | glycyl | H |
| I.3.17 | glycyl | methyl |
| I.3.18 | arginyl | H |
| I.3.19 | arginyl | methyl |
| I.3.20 | glutamyl | H |
| I.3.21 | glutamyl | methyl |
| I.3.22 | lysyl | H |
| I.3.23 | lysyl | methyl |
| I.3.24 | asparagyl | H |
| I.3.25 | asparagyl | methyl |
| I.3.26 | sarcosyl | H |
| I.3.27 | sarcosyl | methyl |
| I.3.28 | acetyl | H |
| I.3.29 | propionyl | H |
| I.3.30 | butanoyl | H |
| I.3.31 | pivaloyl | H |
| I.3.32 | pentanoyl | H |
| I.3.33 | hexanoyl | H |
| I.3.34 | benzoyl | H |
| I.3.35 | phenylacetyl | H |
| I.3.36 | 3-phenylpropionyl | H |
| I.3.37 | 3,3-dimethylbutanoyl | H |

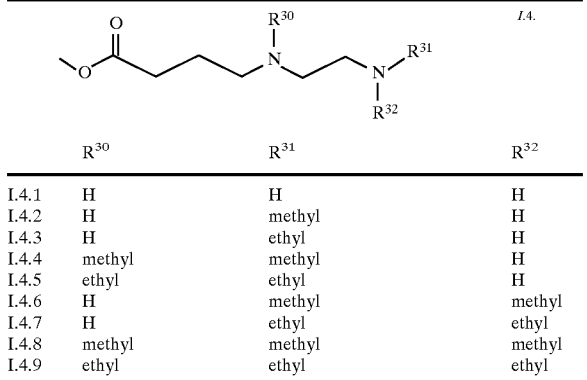

I.4.

| | R$^{30}$ | R$^{31}$ | R$^{32}$ |
|---|---|---|---|
| I.4.1 | H | H | H |
| I.4.2 | H | methyl | H |
| I.4.3 | H | ethyl | H |
| I.4.4 | methyl | methyl | H |
| I.4.5 | ethyl | ethyl | H |
| I.4.6 | H | methyl | methyl |
| I.4.7 | H | ethyl | ethyl |
| I.4.8 | methyl | methyl | methyl |
| I.4.9 | ethyl | ethyl | ethyl |

Particularly preferred compounds according to the invention are those in which W(OH)$_a$ is F.15, which is mono- or disubstituted by a radical of the formula I.1., in which R$^{30}$ is hydrogen, C$_1$–C$_4$-alkyl, CH$_2$P(O)Me$_2$, CH$_2$—CO$_2$H or CH$_2$CO$_2$t-but, R$^{31}$ is hydrogen, or C$_1$–C$_4$-alkyl which is optionally substituted by NH$_2$ or NH(C$_1$–C$_3$)-alkyl; or Arg, Gly, Sar, Lys, Pro, His, Trp, —(CH$_2$)$_3$—N(Me)CH$_2$—CH$_2$NHMe, CH$_2$P(O)Me$_2$, CH$_2$CO$_2$t-Bu or CH$_2$CO$_2$H and R$^{32}$ is hydrogen or C$_1$–C$_4$-alkyl, or is mono- or disubstituted by a radical of the formula I.2., in which R$^{30}$ is hydrogen or C$_1$–C$_3$-alkyl, R$^{31}$ is hydrogen, C$_1$–C$_3$-alkyl, 2(methylamino)-ethyl, Arg or —(CH$_2$)$_2$N(Me)(CH$_2$)$_3$—NH$_2$ and R$^{32}$ is hydrogen or C$_1$–C$_3$-alkyl, or is mono- or disubstituted by a radical of the formula I.3., in which R$^{31}$ is hydrogen, Gly, Leu or (C$_1$–C$_5$)-alkanoyl which is optionally substituted by phenyl or up to 3 methyl groups and R$^{32}$ is hydrogen or C$_1$–C$_3$-alkyl, or is mono- or disubstituted by a radical of the formula I.4., in which R$^{30}$ is C$_1$–C$_3$-alkyl, R$^{31}$ is C$_1$–C$_3$-alkyl and R$^{32}$ is C$_1$–C$_3$-alkyl or hydrogen.

Compounds which may furthermore be mentioned as examples are the following compounds of the formula I W'-[R$^5$]$_a$, in which W' is the enzyme inhibitor on which the compound is based.

1) a=1; W'=F.15, in each case with I.1.1 to I.1.85, I.2.1 to I.2.85, I.3.1 to I.3.37 and I.4.1 to I.4.9
2) a=2; W'=F.15, in each case with I.1.1 to I.1.85, I.2.1 to I.2.85, I.3.1 to I.3.37 and I.4.1 to I.4.9
3) a=1; W'=F.1, F.2, F.4, F.5 (n=1), F.5 (n=2), F.7, F.11, F.12, F.16, F.17 and F.19 in each case
    with: I.1.2, I.1.8, I.1.14, I.1.15, I.1.16, I.1.17, I.1.29, I.1.31, I.1.55, I.1.66, I.1.71, I.1.83, I.1.85,
        I.2.17, I.2.18, I.2.44, I.2.45, I.2.70, I.2.71, I.2.82, I.2.83, I.3.2, I.3.3,
        I.3.4, I.3.16, I.3.30, I.3.36, I.3.37,
            I.4.4, I.4.5, I.4.8, I.4.9
4) a=2; W'=F.3, F.4, F.5 (n=2), F.12 in each case
    with: I.1.2, I.1.14, I.1.15, I.1.16, I.1.17, I.1.31, I.1.55, I.1.66, I.1.71, I.1.82, I.1.84,
        I.2.17, I.2.18, I.2.44, I.2.45, I.2.70, I.2.71, I.2.82, I.2.83,
        I.3.2, I.3.3, I.3.4, I.3.16, I.3.30, I.3.36, I.3.37,
            I.4.4, I.4.5, I.4.8, I.4.9
5) a=3; W'=F.8 in each case
    with: I.1.2, I.1.14, I.1.15, I.1.16, I.1.17, I.1.31, I.1.55, I.1.66, I.1.71, I.1.82, I.1.84,
        I.2.17, I.2.18, I.2.44, I.2.45, I.2.70, I.2.71, I.2.82, I.2.83,
        I.3.2, I.3.3, I.3.4, I.3.16, I.3.30, I.3.36, I.3.37,
            I.4.4, I.4.5, I.4.8, I.4.9

Especially preferred compounds are those in which $W(OH)_a$ is the compound of the formula F.15, which is mono- or disubstituted by a radical of the formula I.1. or I.2. in which $R^{30}$ is H or $(C_1–C_3)$-alkyl, $R^{31}$ is H or $(C_1–C_3)$-alkyl which is optionally substituted by $NH_2$ or $NH(C_1–C_3)$-alkyl and $R^{32}$ is H or $CH_3$.

The invention furthermore relates to the pharmacologically tolerated salts of the compounds of the formula I, for example hydrochlorides, hydrobromides, citrates, tartrates, ethanesulfonates, fumarates, glucuronates, sulfates, isopropane sulfonates, malonates, gluconates, lactates, methanesulfonates, tosylates, tartrates and propanesulfonates.

The present invention furthermore relates to a process for the preparation of the compounds of the formula Ia, which comprises reacting an active compound of the formula $W—(OH)_b$, in which W is as defined above and b can be 1, 2 or 3, but is greater than or equal to a, with A) a compound of the formula (X)

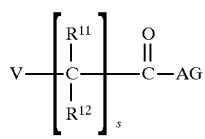

to give a compound of the formula (XX)

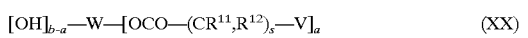

and then

B) reacting the resulting compound of the formula (XX) in turn with nucleophiles of the formulae (XI), (XII) or (XIII)

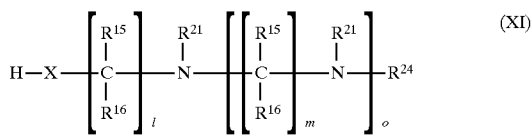

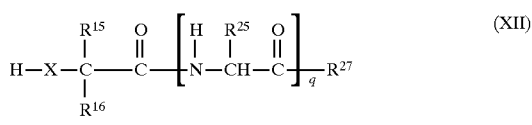

in which W, a, b, X, $R^{11}$, $R^{12}$, $R^{15}$, $R^{16}$, $R^{21}$, $R^{24}$, $R^{25}$, $R^{27}$, l, m, n, o, q, r and s have the abovementioned meanings, V is a suitable leaving group, preferably Br, Cl or OTs, particularly preferably Br, and AG is a leaving group which is suitable for esterification, preferably Br or Cl, or a group such as results from the active ester methods for carboxylic acids (Bodanszky, Peptide Research, Volume 3, 1992, pages 134 to 139).

Step A of the abovementioned process is carried out in an organic solvent, such as acetonitrile, THF or ethyl acetate (EA). The monoacylations are carried out with or preferably without base catalysis or with the addition of a molecular sieve, and the bisacylations are carried out in the presence of a base, preferably N-ethyl-diisopropylamine and/or 4-dimethylaminopyridine (DMAP), or by addition of a molecular sieve, preferably at –78° C. to 66° C., particularly preferably at 0° to 40° C. Working up is carried out by processes known per se, by extraction, chromatography, recrystallization, precipitation and the like.

Step B of the abovementioned process is likewise carried out in an organic solvent, such as, for example, THF, EA or dimethylformamide (DMF) in acetonitrile, preferably at –78° to 82° C., particularly preferably at 0° to 40° C., if appropriate with the addition of iodide.

Protective groups which are still contained in the molecule after the substitution, preferably benzyloxycarbonyl (Z), methoxytrityl (Mtr), tert-butyloxycarbonyl (BOC) and O-tert-butyl ester (OtBu) are split off by standard processes (Greene, Protective Groups in Organic Synthesis, Wiley 1979). Working up is likewise carried out by processes known per se, by extraction, chromatography, recrystallization, precipitation and the like.

The compounds of the formulae 1 to 15 are prepared in accordance with the sources cited for these compounds.

The compounds of the formulae XI to XIII are commercially obtainable (for example Aldrich Chemie GmbH & Co. KG, Steinheim) or can be synthesized by generally known methods, for example in accordance with Beilstein, Handbuch der organischen Chemie [Handbook of Organic Chemistry], Volume IV and supplements, Springer Verlag Berlin, Heidelberg, New York or Houben-Weyl, Methoden der organischen Chemie [Methods of Organic Chemistry], Volumes 11/1, 11/2 and E 16d2, Thieme Verlag Stuttgart, Helv. Chim. Acta 74, 654 et seq. (1991), J. Med. Chem 34, 2, 269 et seq. (1991) or Greene loc. cit. or in accordance with the literature cited in the abovementioned documents.

On the basis of their properties, the novel compounds according to the invention are particularly suitable for administration in the form of sterile aqueous solutions by means of intravenous injection, intravenous infusion or intramuscular or subcutaneous injection or for topical use on the eye. Because of their good solubility at acid pH values, these prodrugs are also beneficial for peroral administration, for example for improving the bioavailability of starting active compounds of low water-solubility which contain a hydroxyl group. On the basis of their solubility and stability properties, the novel prodrugs furthermore are particularly suitable for rectal or dermal administration.

The lipophilicity of the prodrug derivatives of the formula I can easily be modified or controlled by the corresponding choice of substituents in the compounds, both in respect of the amine basicity and correspondingly the degree of ionization at physiological pH values, and in respect of the hydrophobicity of the substituents. Prodrug derivatives of the formula I can therefore be chosen which, owing to a combination of improved water-solubility and lipophilicity, are capable of displaying an improved biomembrane transportation, so that a better bioavailability of the starting active compounds exists from the site of administration.

The compounds according to formula I can be employed for the treatment of any diseases for which the hydroxyl-containing starting active compounds, medicaments and pharmaceuticals are beneficial. The prodrug compounds of the formula I can therefore be administered orally, topically, parenterally, rectally or by means of an inhalation spray, in presentation forms or formulations which comprise conventional, nontoxic, pharmaceutically acceptable carrier substances, auxiliaries and vehicles. The formulation and preparation of any of the presentation forms from this broad spectrum into which the prodrugs according to the invention can be incorporated is known to the expert. Additional information can be found in "Remington's Pharmaceutical Sciences", sixteenth edition, 1980.

The pharmaceutical compositions which comprise the active compound can be in a suitable form for oral administration, for example as tablets, pastilles, lozenges, aqueous suspensions or solutions, dispersible powders or granules, emulsions, hard or soft capsules, syrup or elixir. Compositions intended for oral administration can be prepared by any relevant method corresponding to the prior art for the preparation of pharmaceutical compositions, and these compositions can contain one or more substances from the group consisting of sweeteners, flavorings, dyestuffs and preservatives, in order to is obtain a pharmaceutically elegant formulation which is easy to take.

Formulations for oral administration include tablets which comprise the active compound in a mixture with nontoxic, pharmaceutically acceptable carrier substances. These carrier substances can be, for example, inert extenders (such as, for example, calcium carbonate, sodium chloride, lactose, calcium phosphate or sodium phosphate), granulating or disintegrating agents (for example potato starch or alginic acid), binders (such as, for example, starch, gelatin or gum arabic) and lubricants (such as, for example, magnesium stearate, stearic acid or talc). The tablets can be noncoated or they can be coated by means of the known techniques, in order to delay dissolution and absorption in the gastro intestinal tract and therefore to provide a sustained action over a relatively long period of time. Thus, for example, a time-delaying substance, such as, for example, glyceryl monostearate or glyceryl distearate, can be employed.

Formulations for oral administration can also be made available in the form of hard gelatin capsules in which the active compound is mixed with an inert solid extender, for example calcium carbonate, calcium phosphate or kaolin, or in the form of soft gelatin capsules, in which the active compound is mixed with water or an oily medium, for example peanut oil, liquid paraffin or olive oil.

Typical dosage forms for rectal use of the compounds according to formula I of this invention comprise suppositories, rectal gelatin capsules (solutions and suspensions) and enemas or micro-enemas (solutions and suspensions). In a typical formulation for a suppository, any compound according to the invention is thus combined with a pharmaceutically acceptable suppository base, such as, for example, cacao butter, esterified fatty acids (C10–C18) and glycerolated gelatin, and various water-soluble or dispersible base substances, such as, for example, polyethylene glycols and polyethylene sorbitan fatty acid esters. Various additives, such as salicylates or surfactants, can be included. Enemas or micro-enemas of the solution type can easily be dissolved by dissolving the water-soluble prodrug according to the invention in water or in water-containing, for example 0.5%, methylcellulose or another viscosity-increasing substance.

For topical use, the creams, ointments, gels, solutions or the like comprising the prodrug are used by the methods known as the prior art.

Sterile aqueous solutions of the compounds of the formula I for parenteral administration or ophthalmic use also comprise other constituents, such as preservatives, antioxidants, chelating agents, buffer substances or other stabilizing agents.

The therapeutic dosage spectrum of the compounds according to the invention varies of course according to the size and requirements of the patient and the particular pain or disease symptoms to be treated. In general, however, it can be said that the following recommended dosages are adequate. For oral administration, the therapeutic dosage required for a compound according to the invention corresponds, on a molecular basis, to that required for the hydroxyl-containing starting active compound. In the case of topical use, application of a compound according to the invention in a concentration of 0.01% to 5% (in a suitable topical carrier material) to the affected area is probably sufficient.

The amount of active compound which can be combined with carrier substances in order to form a single presentation form varies according to the host to be treated and the particular type of administration. Thus, for example, a formulation for oral administration intended for humans can comprise between 5 mg and 5 g of the active compound with an appropriate and expedient amount of carrier substances, which can make up between 5 and 95% of the total composition. Other presentation forms, such as, for example, ophthalmic presentation forms, comprise a smaller content of the active compound, for example between 0.1 mg and 5 mg. Dosage units in general comprise between about 0.1 mg and 500 mg of the active compound.

It goes without saying that the specific dosage for each individual patient depends on a large number of factors, including the activity of the specific compound which is employed, age, body weight, general state of health, sex, diet, time of administration, administration route, rate of excretion, interactions with other medicaments and severity of the particular illness treated.

Examples

Example 1

Figure 1B:
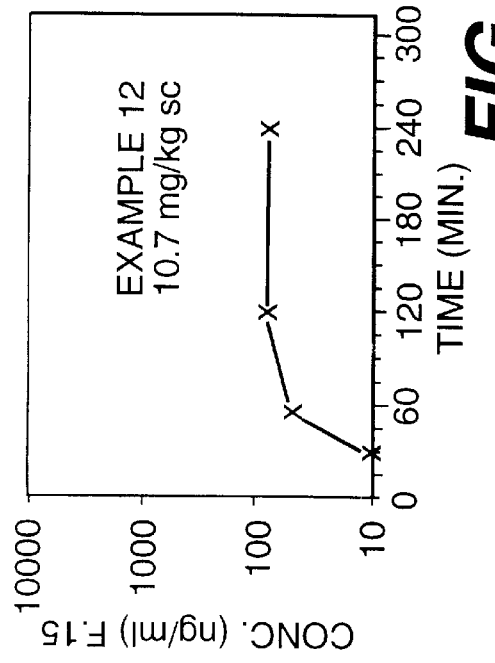
FIG. 1B shows the serum concentration of the active compound F.15 plotted against time following subcutaneous administration of F.15 and the compound described in Example 12 to NMRI mice.
Figure 1D:
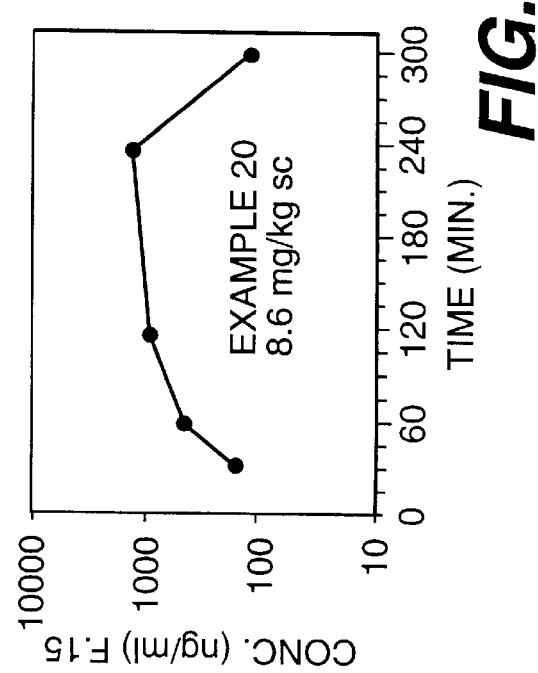
FIG. 1D shows the serum concentration of the active compound F.15 plotted against time following subcutaneous administration of F.15 and the compound described in Example 20 to NMRI mice.
Figure 1A:
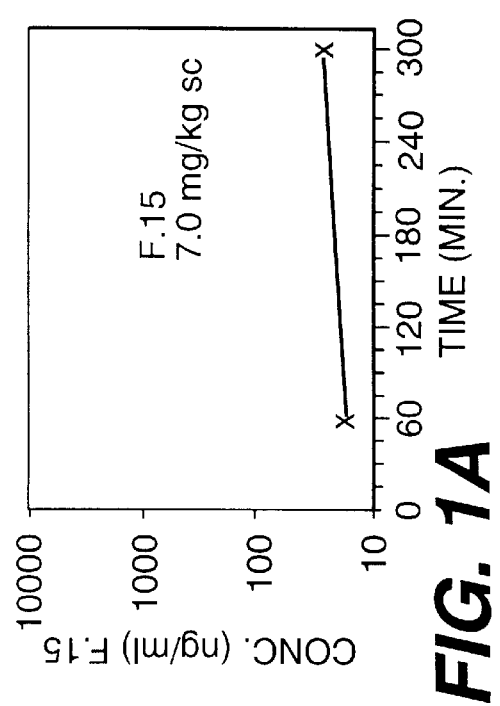
FIG. 1C shows the serum concentration of the active compound F.15 plotted against time following subcutaneous administration of F.15 and the compound described in Example 13 to NMRI mice.
FIG. 1E shows the serum concentration of the active compound F.15 plotted against time following subcutaneous administration of F.15 and the compound described in Example 25 to NMRI mice.
FIG. 1F shows the serum concentration of the active compound F.15 plotted against time following subcutaneous administration of F.15 and the compound described in Example 26 to NMRI mice.
FIG. 1G shows the serum concentration of the active compound F.15 plotted against time following subcutaneous administration of F.15 and the compound described in Example 24 to NMRI mice.
FIG. 1H shows the serum concentration of the active compound F.15 plotted against time following subcutaneous administration of F.15 and the compound described in Example 17 to NMRI mice.
Figure 1C:
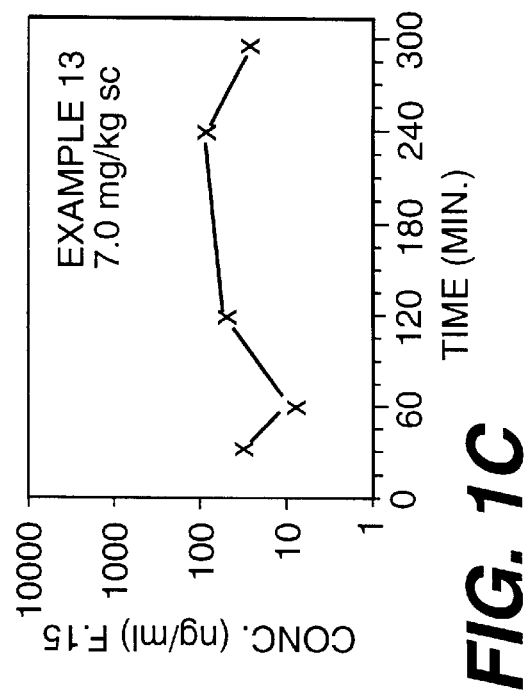

| $R^5$ = OCOCH$_2$Br |
| bromoacetoxy |
| $R^{5*}$ = OH |
| W = F.15 |

610 mg of dimethylaminopyridine and a solution of 400 mg of bromoacetyl bromide in 1 ml of dry THF were added to 1.13 g of N,N'-bis-[(2S-(1,1-dimethylethylsulfonylmethyl)-3-(1-naphthyl)-propionyl)-L-valyl]-2S,5S-diamino-1,6-diphenyl-hexane-3R,4R-diol ($R^5$=$R^{5*}$=OH) in 25 ml of dry THF under argon at 0° C. in the course of 10 minutes. After the mixture had been stirred at 0° C. for 20 minutes, it was allowed to come to RT and the solvent was removed in vacuo at RT. The residue was dissolved in EA and the solution was extracted by shaking with KHSO$_4$ (3×) and then with NaCl solution. The organic phase was concentrated in vacuo and the residue was purified over silica gel (toluene:EA 1:1 to 2:1).

Yield: 340 mg NMR (270 MHz, CDCl3): 0.57(d, 7 Hz, 3H); 0.69–0.80 (m, 9H); 1.23 (s, 9H); 1.33 (s, 9H); 2.07 (m, 2H); 2.56 (dd, 14 Hz, 8 Hz, 1H); 2.70–2.97 (m, 3H); 3.09 (dd, 14 Hz, 2 Hz, 1H); 3.17 (dd, 14 Hz, 3 Hz, 1H); 3.28–3.60 (m, 9H); 3.75–3.90 (m, 3H); 4.08 (s, 2H); 4.25 (m, 1H); 4.58 (m, 1H); 4.88 (d, 9 Hz, 1H); 5.68 (d, 8 Hz, 1H); 5.86 (d, 8 Hz, 1H); 6.09 (d, 8 Hz, 1H); 6.19 (d, 10 Hz, 1H); 6.98 (m, 2H); 7.08–7.44 (m, 12H); 7.52 (m, 2H); 7.63 (m, 2H); 7.74–7.94 (m, 4H); 8.09 (d, 8 Hz, 1H); 8.15 (d, 8 Hz, 1H) MS(FAB): [1253.7, 1251.7](M+H)$^\oplus$, 1235.6, 1233.6

Example 2

| $R^5$ = OCOCH$_2$Br |
| bromoacetoxy |
| $R^{5*}$ = $R^5$ |
| W = F.15 |

Method A:
10 g of N,N'-bis-[(2S-(1,1-dimethylethylsulfonylmethyl)-3-(1-naphthyl)-propionyl)-L-valyl]-2S,5S-diamino-1,6-diphenyl-hexane-3R,4R-diol ($R^5$ =$R^{5*}$=OH) were suspended in 100 ml of toluene, and 3.2 g of DMAP in 10 ml of toluene were added. 10.7 g of bromoacetyl bromide in 10 ml of toluene were added dropwise at −20° C., while stirring. 70 ml of acetonitrile were added and the mixture was stirred at RT for 7 hours. The slightly cloudy solution was diluted with EA and washed with ice-cold 0.5N HCl (2×), NaHCO$_3$ solution (2×) and NaCl solution, dried over anhydrous MgSO$_4$ and concentrated in vacuo. The residue was purified over silica gel (toluene: EA 1:1) and gave 12.6 g of product.

Method B: 5 g of N,N'-bis-[(2S-(1,1-dimethylethylsulfonylmethyl)-3-(1-naphthyl)-propionyl)-L-valyl]-2S,5S-diamino-1,6-diphenyl-hexane-3R,4R-diol ($R^5$ =$R^{5*}$=OH) were stirred with 2.5 g of dry and powdered molecular sieve 4 Å, in 80 ml of dry EA at RT. 2.35 ml of bromoacetyl bromide were slowly added and the mixture was stirred at RT for 6 hours. The molecular sieve was filtered off with suction and the organic solution was washed with water (2×) and NaHCO$_3$ solution. It was dried over anhydrous MgSO$_4$ and the solvent was removed in vacuo. The residue was taken up in toluene and the mixture was concentrated again in vacuo. After drying, 6.4 g of product were obtained.

NMR (270 MHz, DMSO<D6>): 0.83 (d, 7 Hz, 6H); 0.88 (d, 7 Hz, 6H); 1.06 (s, 18H); 1.92 (m, 2H); 2.60–2.77 (m, 6H); 3.05 (dd, 10 Hz, 14 Hz, 2H); 3.21 (dd, 14 Hz, 5 Hz, 2H); 3.41 (m, 2H); 3.63 (dd, 14 Hz, 9 Hz, 2H); 4.02–4.15 (m, 2H); 4.20 (m, 2H); 5.07 (m, 2H); 5.14 (s, 2H); 6.98 (m, 2H); 7.12–7.45 (m, 12H); 7.49–7.64 (m, 4H); 7.83 (m, 2H); 7.88–7.98 (m, 4H); 8.20 (d, 8 Hz, 4H); MS(FAB): [1375.6, 1373.6, 1371.6](M+H)$^\oplus$

Example 3

| $R^5$ = OCOCH$_2$Cl |
| chloroacetoxy |
| $R^{5*}$ = OH |
| W = F.15 |

1.13 g of N,N'-bis-[(2S-(1,1-dimethylethylsulfonylmethyl)-3-(1-naphthyl)-propionyl)-L-valyl]-2S,5S-diamino-1,6-diphenyl-hexane-3R,4R-diol ($R^5$=$R^{5*}$=OH) were dissolved in 25 ml of dry THF, and 610 mg of DMAP were added. 120 μl of chloroacetyl chloride in 1 ml of THF were added dropwise at 0° C. and the mixture was stirred at 0° C. for 10 minutes. It was allowed to warm to RT and was diluted with 100 ml of EA and extracted with KHSO$_4$ solution. The EA phase was dried over MgSO$_4$ and concentrated in vacuo and the residue was chromatographed over silica gel (EA:toluene 1:1 to 1.5:1). 644 mg of monoacylation product were obtained.

NMR (270 MHz, CDCl3): 0.56 (d, 7 Hz, 3H); 0.69–0.80 (m, 9H); 1.23 (s, 9H); 1.34 (s, 9H); 2.06 (m, 2H); 2.54 (dd, 14 Hz, 8 Hz, 1H); 2.68–2.97 (m, 3H); 3.09 (dd, 14 Hz, 2 Hz, 1H); 3.18 (dd, 14 Hz, 3 Hz, 1H); 3.28–3.60 (m, 9H); 3.82

(m, 2H); 4.08 (m, 3H); 4.24 (m, 1H); 4.58 (m, 1H); 4.89 (d, 9 Hz, 1H); 5.68 (d, 8 Hz, 1H); 5.86 (d, 8 Hz, 1H); 6.05 (d, 8 Hz, 1H); 6.21 (d, 10 Hz, 1H); 6.97 (m, 2H); 7.08–7.44 (m, 12H); 7.53 (m, 2H); 7.63 (m, 2H); 7.74–7.94 (m, 4H); 8.08 (d, 8 Hz, 1H); 8.15 (d, 8 Hz, 1H). MS(FAB): [1209.6, 1207.6](M+H)$^\oplus$; 1191.6, 1189.6

Example 4

| |
|---|
| $R^5$ = OCOCH$_2$Cl chloroacetoxy |
| $R^{5*}$ = $R^5$ |
| W = F.15 |

1.13 g of N,N'-bis-[(2S-(1,1-dimethylethylsulfonyl-methyl)-3-(1-naphthyl)-propionyl)-L-valyl]-2S,5S-diamino-1,6-diphenyl-hexane-3R,4R-diol ($R^5$=$R^{5*}$=OH) were dissolved in 25 ml of dry THF, and 1.22 g of DMAP were added. 320 μl of chloroacetyl chloride in 5 ml of THF were added dropwise at 0° C.. The mixture was stirred at 0° C. for 2 h, and a further 150 μl of chloroacetyl chlor- ide were added. After 30 minutes, the THF was removed in vacuo, the residue was taken up in EA and the mixture was extracted with KHSO$_4$ solution and dried over MgSO$_4$. The solvent was distilled off in vacuo and the residue was purified over silica gel (EA:toluene 1:2 to 1:1). 815 mg of bisacylation product were obtained.

NMR (270 MHz, CDC13): 0.75 (d, 7 Hz, 6H); 0.82 (d, 7 Hz, 6H); 1.27 (s, 18H); 1.98 (m, 2H); 2.56 (dd, 8 Hz, 14 Hz, 2H); 2.84 (dd, 14 Hz, 5 Hz, 2H); 3.30–3.45 (m, 6H); 3.51 (dd, 13 Hz, 7 Hz, 2H); 3.93 (s, 4H); 4.07 (m, 2H); 5.00 (m, 2H); 5.18 (s, 2H); 5.95 (d, 9 Hz, 2H); 6.07 (d, 8 Hz, 2H); 7.07–7.28 (m, 12H); 7.35 (t, 8 Hz, 2H); 7.52 (t, 8 Hz, 2H); 7.61 (m, 2H); 7.77 (d, 8 Hz, 2H); 7.88 (d, 8 Hz, 2H); 8.10 (d, 8 Hz, 2H). MS(FAB): [1287.5, 1285.5, 1283.5](M+H)$^\oplus$ Example 5

| |
|---|
| $R^5$ = OCOC(Me)$_2$Br α-bromo-isobutyryloxy |
| $R^{5*}$ = OH |
| W = F.15 |

2.26 g of N,N'-bis-[(2S-(1,1-dimethylethylsulfonyl-methyl)-3-(1-naphthyl)-propionyl)-L-valyl]-2S,5S-diamino-1,6-diphenyl-hexane-3R,4R-diol ($R^5$=$R^{5*}$=OH) were stirred with 1.48 g of DMAP and 2.76 of α-bromo-isobutyric acid bromide in 10 ml of THF at RT for 120 hours. The mixture was diluted with EA and washed with ice-cold 0.5N HCl (2×), NaHCO$_3$ solution (2×) and NaCl solution. It was dried over anhydrous MgSO$_4$ and concentrated in vacuo and the residue was purified by chromatography over silica gel (toluene:EA 4:1 to 1:1). 1.7 g of product were obtained.

MS(FAB): [1282.5, 1281.5, 1280.5, 1279.5] (M+H)$^\oplus$, 1264.5, 1263.5, 1262.5, 1261.5

Example 6

| |
|---|
| $R^5$ = OCOCH$_2$N(Et)(CH$_2$)$_2$N(Et)$_2$ [N-ethyl-N-(2-diethylaminoethyl)-amino]-acetoxy |
| $R^{5*}$ = $R^5$ |
| W = F.15 |

128 mg of the compound Example 4 were stirred in 2 ml of dry THF with 87 mg of N,N'-triethylethylenediamine at 50° C. for 16 hours. The reaction solution was taken up in 50 ml of EA, the mixture was extracted against KHCO$_3$/NaCl solution, the organic phase was dried with Na$_2$SO$_4$ and filtered and the solvent was distilled off in vacuo. The crude product was purified over silica gel (CH$_3$OH:triethylamine 98:2).

The yield was: 40 mg MS(FAB): 1500.0 (M+H)$^\oplus$, 1315.8, 750.5

Example 7

| |
|---|
| $R^5$ = OCOCH$_2$N(Et)(CH$_2$)$_2$N(Et)$_2$ [N-ethyl-N-(2-diethylaminoethyl)-amino]-acetoxy |
| $R^{5*}$ = OH |
| W = F.15 |

121 mg of the compound Example 3 were reacted analogously to Example 6.

Yield: 52 mg MS(FAB): 1315.8 (M+H)$^\oplus$

Example 8

| |
|---|
| $R^5$ = OCOCH$_2$N(Me)(CH$_2$)$_2$N(Me)COOCMe$_3$ [N-methyl-N-{2-(N-tert-butoxycarbonyl-N-methyl)-aminoethyl}-amino]-acetoxy |
| $R^{5*}$ = OH |
| W = F.15 |

113 mg of N-(t-butoxycarbonyl)-N,N'-dimethyl-ethylenediamine (Example 8-a) were added to 121 mg of the compound Example 3 in 1 ml of dry THF at RT. The mixture was stirred at 50° C. for 16 hours. The THF was distilled off, the residue was taken up in EA and the mixture was extracted by shaking 2× with KHCO$_3$ solution, dried with MgSO$_4$ and concentrated in vacuo. The residue was purified over silica gel (DCM:CH$_3$OH 98:2 to 90:10). The yield was 95 mg.

MS(FAB): 1359.7 (M+H)$^\oplus$ a) Preparation of N-(tert-butoxycarbonyl)-N,N'-dimethyl-ethylenediamine 8.8 g of N,N'-dimethylethylenediamine were dissolved in 50 ml of ether and the solution was cooled to 0° C. 18.5 g of BOC-ON [2-(tert-butoxycarbonyloxyimino)-2-phenylacetonitrile] were slowly added dropwise and the mixture was stirred at RT for 16 hours. 6 g of sodium methylate were added and stirring was continued at RT for 18 hours. The substance which had precipitated out was filtered off with suction and washed with ether. The combined ether solution was concentrated in vacuo and the residue was distilled (boiling point 58°–60° C./0.5 mbar). 11.3 g were obtained as a colorless oil. MS(Cl): 189 (M+H)$^\oplus$, 133

Example 9

| |
|---|
| $R^5$ = OCOCH$_2$N(Me) (CH$_2$)$_2$NHMe [N-methyl-N-(2-methylaminoethyl)-amino]-acetoxy (as the HCl salt) |
| $R^{5*}$ = OH |
| W = F.15 |

3 ml of 5N HCl in dimethoxyethane were added to 75 mg of the compound Example 8 and the mixture was stirred at RT for 1 hour. The solvent was then distilled off in vacuo and the oily residue was triturated several times with ether.

Yield: 55 mg MS(FAB): 1259.7 (M+H)$^{\oplus}$

Example 10

$R^5$ = OCOCH$_2$NH(CH$_2$)$_3$NHCOOC(Me)$_3$
[N-{3-N-tert-butoxycarbonyl)-aminopropyl}-amino]-acetoxy
$R^{5*}$ = OH
W = F.15

121 mg of the compound Example 3 were reacted with 104 mg of N-(tert-butoxycarbonyl)-1,3-diaminopropane (Example 10-a) analogously to Example 8. The reaction time was 3 hours at 50° C.

Yield: 69 mg MS(FAB): 1345.7 (M+H)$^{\oplus}$ a) Preparation of N-(tert-butoxycarbonyl)-1,3-diaminopropane A solution of 14.7 g of di-tert-butyl dicarbonate in 200 ml of dry dioxane was added to 37 g of 1,3-diaminopropane in 180 ml of dry dioxane at RT in the course of 2 hours. The mixture was stirred at RT for 16 hours. The precipitate which had precipitated out was filtered off with suction and the filtrate was concentrated in vacuo. The residue was then evaporated 3× with 100 ml of toluene each time. The oily residue was suspended in 350 ml of water and the precipitate was filtered off. The filtrate was extracted 4× with 250 ml of DCM each time and then dried with Na$_2$SO$_4$ and concentrated in vacuo. Purification was carried out over silica gel (CH$_3$OH).

Yield: 5 g MS(C$_1$): 175 (M+H)$^{\oplus}$, 119

Example 11

$R^5$ = OCOCH$_2$N(Me) (CH$_2$)$_3$N(Me)COOC(Me)$_3$
[N-methyl-N-{3-(N-tert-butyoxycarbonyl-N-methyl)-aminopropyl}-amino]-acetoxy
$R^{5*}$ = OH
W = F.15

121 mg of the compound Example 3 were reacted with 121 mg of N-tert-butoxycarbonyl-N,N'-dimethyl-1,3-propanediamine (Example 11-a) analogously to Example 10.

Yield: 52 mg MS(FAB): 1373.7 (M+H)$^{\oplus}$ a) Preparation of N-tert-butoxycarbonyl-N,N'-dimethyl-1,3-propanediamine A solution of 2.79 g of di-tert-butyl dicarbonate in 40 ml of dry dioxane was added to 10.2 g of N,N'-dimethyl-1,3-propanediamine in 40 ml of dry dioxane at RT in the course of 2 hours. The mixture was stirred at RT for 16 hours. The solvent was then distilled off in vacuo and the residue was evaporated 2× with toluene. The residue was dissolved in 60 ml of water and the solution was extracted 3× with 50 ml of EA each time. The organic phase was then washed with aqueous KHCO$_3$/NaCl solution, dried with Na$_2$SO$_4$ and concentrated.

Yield: 2.14 g MS(Cl): 203 M+H)$^{\oplus}$, 147

Example 12

$R^5$ = OCOCH$_2$N(Me) (CH$_2$)$_3$NHMe
[N-methyl-N-(3-methylaminopropyl)-amino]-acetoxy (as the HCl salt)
$R^{5*}$ = OH
W = F.15

40 mg of the compound Example 11 were reacted analogously to Example 9.

Yield: 32 mg MS(FAB): 1273.9 (M+H)$^{\oplus}$

Example 13

$R^5$ = OCOCH$_2$NH(CH$_2$)$_3$NH$_2$
[N-(3-aminopropyl)-amino]-acetoxy (as the HCl salt)
$R^{5*}$ = OH
W = F.15

50 mg of the compound Example 10 were reacted analogously to Example 9.

Yield: 35 mg MS(FAB): 1245.8 (M+H)$^{\oplus}$

Example 14

$R^5$ = OCOCH$_2$N(Me)(CH$_2$)$_3$N(Me)COOC(Me)$_3$
[N-methyl-N-{3-(N-tert-butoxycarbonyl-N-methyl)-aminopropyl}-amino]-acetoxy
$R^{5*}$ = $R^5$
W = F.15

193 mg of the compound Example 4 were dissolved with 364 mg of N-tert-butoxycarbonyl-N,N'-dimethyl-1,3-propanediamine (Example 11-a) in 3 ml of dry THF under N$_2$ and the solution was stirred at 50° C. for 16 hours. The solvent was distilled off, the residue was taken up in EA and the mixture was extracted by shaking with KHCO$_3$ solution and KHSO$_4$ solution. The organic phase was dried with Na$_2$SO$_4$ and concentrated. Purification was carried out over silica gel (EA:CH$_3$OH 98:2 to 90:10).

Yield: 183 g MS(FAB): 1615.8 (M+H)$^{\oplus}$

Example 15

$R^5$ = OCOCH$_2$N(Me)(CH$_2$)$_3$NHMe
[N-methyl-N-(3-methylaminopropyl)-amino]-acetoxy (as the HCl salt)
$R^{5*}$ = $R^5$
W = F.15

150 mg of the compound Example 14 were reacted analogously to Example 9.

Yield: 121 mg MS(FAB) : 1415.8 (M+H)$^{\oplus}$

Example 16

$R^5$ = OCOCH$_2$N(Me)(CH$_2$)$_2$N(Me)COOC(Me)$_3$
[N-methyl-N-{2-(N-tert-butoxycarbonyl-N-methyl)-aminoethyl}-amino]-acetoxy
$R^{5*}$ = $R^5$
W = F.15

3.6 g of the compound Example 4 were stirred with 1.24 ml of N-butoxycarbonyl-N,N'-dimethylethylendiamine and 1.06 ml of N-ethyl-diisopropylamine in 40 ml of EA at RT for 20 hours. The mixture was extracted with 5% strength aqueous citric acid solution (2×), water, NaHCO$_3$ solution (2×) and NaCl solution. After drying over anhydrous MgSO$_4$, the solvent was distilled off in vacuo. The residue was purified with EA over silica gel, which had been deactivated beforehand with 10% of water. 3.15 g of product were obtained. MS(FAB): 1587.9 (M+H)$^{\oplus}$

Example 17

$R^5$ = OCOCH$_2$N(Me)(CH$_2$)$_2$NHMe
[N-methyl-N-(3-methylaminoethyl)-amino]-acetoxy
(as the HCl salt)
$R^{5*}$ = $R^5$
W = F.15

110 mg of the compound Example 16 were reacted with 5N HCl in dioxane analogously to Example 9.

Yield: 85 mg MS(FAB): 1387.7 (M+H)$^⊕$

Example 18

$R^5$ = OCOCH$_2$N(Me)(CH$_2$)$_2$N(Me) (CH$_2$)$_3$N(Me) (CH$_2$)$_2$NHMe
[(3,6,10-trimethyl-3,6,10,13-tetraaza-tetra-decanoyloxy]
$R^{5*}$ = OH
W = F.15

A solution of 29 mg of 5,9-dimethyl-(2,5,9,12-tetraaza)-tridecane (Example 18-a) in 1.5 ml of dry DMF was added to 125 mg of the compound Example 1 in 1.5 ml of dry DMF at RT. 26 mg of N-ethyl-diisopropylamine were then added. The mixture was stirred at 50° C. for 5 hours. The reaction solution was distilled in vacuo and the residue was taken up in DCM. The mixture was extracted by shaking 2× with aqueous KHSO$_4$ solution and then washed with saturated NaCl solution. The organic phase was dried with MgSO$_4$ and evaporated. The residue was digested several times with ether.

Yield: 101 mg MS(FAB): 1387.8 (M+H)$^⊕$ a) Preparation of 5,9-dimethyl-(2,5,9,12-tetraaza)-tridecane (as the HCl salt)

208 mg of 2,12-di-tert-butoxycarbonyl-5,9-dimethyl-(2,5,9,12-tetraaza)-tridecane (Example 18-b) were reacted analogously to Example 9.

Yield: 160 mg NMR (200 MHz, DMSO<D6>): 2.15(m, 2H); 2.54(s, 6H); 2.76(s, 6H); 3.1–3.5(m, about 14H); 9.4(m, br, about 4H). MS(Cl): 217 (M+H)$^⊕$, 172 b) Preparation of 2,12-di-tert-butoxycarbonyl-5,9-dimethyl-(2,5,9,12-tetraaza)-tridecane 414 mg of N-(t-butoxycarbonyl)-N,N'-dimethyl-ethylenediamine (Example 8-a) were kept under reflux in 10 ml of dry EtOH with 202 mg of 1,3-dibromopropane, with the addition of 253 mg of N-ethylmorpholine, for 6 hours. The reaction mixture was then stirred with 185 mg of propionyl chloride at RT for 30 minutes, and 10 ml of water were subsequently added. After a further 30 minutes, the mixture was diluted with EA and extracted with aqueous KESO$_4$ solution. The aqueous phase was brought to pH: 7–8 with solid NaHCO$_3$ and then extracted 2× with EA, and the combined organic phases were dried with Na$_2$SO$_4$. filtered and concentrated in vacuo. The crud e product was purified over silica gel (DCM:MeOH 95:5).

Yield: 225 mg NMR (200 MHz, CDCh13): 1.48(s, 18H); 1.63(quint, 2H); 2.26(s, 6H); 2.33–2.58(m, 8H); 2.88(s, 6H); 3.31(m, 4H). MS(Cl): 417 (M+H)$^⊕$, 317, 272

Example 19

$R^5$ = OCOCH$_2$N(Me) (CH$_2$)$_2$N(Me)$_2$
N-(2-dimethylamino-ethyl)-N-methyl-amino-acetoxy (as the HCl salt)
$R^{5*}$ = $R^5$
W = F.15

94 mg of the compound Example 4 were dissolved in 2.5 ml of dry DMF, and 84 mg of N,N,N'-trimethylethylenediamine and a spatula-tip of XI were added at RT. The mixture was stirred at RT for 3 days and at 60° C. for 8 hours. The solvent was distilled off in vacuo, the residue was taken up in EA and the mixture was washed with saturated KHCO$_3$ solution (2×) and NaCl solution, dried over MgSO$_4$ and concentrated in vacuo. Chromatography over silica gel (DCM:MeOH 8:2 to 1:1, then DCM:MeOH:NEt$_3$ 15:15:1) gave 21 mg of product, which was converted in the hydrochloride by treatment with 0.1N ethanolic HCl. MS(FAB): 1415.8 (M+H)$^⊕$

Example 20

$R^5$ = OCOCH$_2$NH(CH$_2$)$_3$N(Me) (CH$_2$)$_2$N(Me) (CH$_2$)$_3$NH$_2$
7,10-dimethyl-3,7,10,14-tetraaza-tetradecanoyl
(as the HCl salt)
$R^{5*}$ = OH
W = F.15

204 mg of the compound Example 3 were stirred with 250 mg of N-(3-aminopropyl)-N'-(3-tert-butoxycarbonylamino-propyl)-N,N'-dimethyl-ethylenediamine (Example 20-a) in 5 ml of acetonitrile and a spatula-tip of KI at RT for 16 hours. The mixture was concentrated in vacuo and the residue was partitioned between EA and KHCO$_3$ solution. The organic phase was dried and concentrated in vacuo. Chromatography over silica gel (EA:MeOH:triethylamine 90:10:0.2 to 80:20:1) gave 86 mg of product still protected by tert-butoxycarbonyl [MS(FAB): 1474.2 (M+H)$^⊕$], from 33 mg of which the protective groups were removed by treatment with 6N HCl in dioxane analogously to Example 9, the product being converted into the salt. 34 mg of product were obtained.

MS(FAB): 1373.8 (M+H)$^⊕$ a) Preparation of N-(3-aminopropyl)-N'-(3-tert-butoxy-carbonylaminopropyl)-N,N'-dimethyl-ethylenediamine 5.3 g of acrylonitrile were slowly added to 4.4 g of N,N'-dimethyl-ethylenediamine, while cooling with ice. The mixture was allowed to warm slowly to RT and was stirred at RT for 14 hours. It was heated at 80° C. for 3 hours and the volatile constituents were then removed in vacuo at a bath temperature of 80° C. 9.6 g of N,N'-bis-(2-cyanoethyl)-N,N'-dimethyl-ethylenediamine were obtained.

MS (Cl): 195 (M+H)$^⊕$, 154

9.5 g of this product were dissolved in 35 ml of glacial acetic acid and 35 ml of concentrated HCl, while cooling. After addition of 0.4 g of PtO$_2$, hydrogenation was carried out at RT under 5 atmospheres of H$_2$ for 24 hours. After the catalyst had been filtered off, the filtrate was concentrated in vacuo, and the residue was taken up in ethanol and the mixture concentrated in vacuo again several times. The residue was then stirred with ethanol, the ethanol was decanted and the residue was dried in vacuo. N,N'-bis-(3-Aminopropyl)-N,N'-dimethyl-ethylenediamine was obtained as the salt.

MS(Cl): 203 (M+H)$^⊕$ 9.81 g of this product were dissolved in 200 ml of dioxane/water (1:1), and 141 ml of 1N NaOH were added at 0° C. and 3.70 g of di-tert-butyldicarbonate in 25 ml of dioxane were subsequently added over a period of 2 hours. The mixture was stirred at 0° C. for 1 hour and at RT for 2 hours. The dioxane was distilled off in vacuo and the residue was partitioned between EA and $K_2CO_3$ solution. The organic phase was dried, filtered and concentrated in vacuo. 4.4 g of N-(3-aminopropyl)-N-(3-tert-butoxycarbonylamino-propyl)-N,N'-dimethyl-ethylenediamine were obtained and were purified as follows:

750 mg of N-(benzoxycarbonyloxy)-succinimide in 30 ml of THF were slowly added to 0.7 g of the product, dissolved in 30 ml of THF, at 0° C. The mixture was stirred at 0° C. for 1 hour, and at RT for 1 hour, the solvent was removed in vacuo and the residue was partitioned between EA and $KHCO_3$ solution. The organic phase was dried ($Na_2SO_4$) and concentrated in vacuo. Chromatography over silica gel (EA:MeOH 8:2, 1% of triethylamine) gave 0.38 g of N-(3-tert-butoxycarbonylamino-propyl)-N'-(3-carbobenzoxycarbonyl-amino-propyl)-N,N'-dimethyl-ethylenediamine.

NMR (200 MHz, $CDCl_3$): 1.42 (s, 9H); 1.50–1.70 (m, 4H); 2.1–2.5 (m, 14H); 3.05–3.35 (m, 4H); 5.1 (s, 2H); about 6.15 (br, 2H); 7.3–7.4 (m, 5H). MS(Cl): 437 $(M+H)^⊕$, 337

0.36 g of the product was dissolved in 30 ml of MeOH, and 100 ml of Pd (10% strength in charcoal) were added. The mixture was stirred at RT under 1 atmosphere of $H_2$ for 2 hours. After removal of the catalyst by filtration, 0.25 g of the desired amine was obtained.

Example 21

$R^5$ = $OCOCH_2NH(CH_2)_3N(Me)$ $(CH_2)_2N(Me)$ $(CH_2)_3NH_2$
7,10-dimethyl-3,7,10,14-tetraaza-tetradecanoyl
(as the HCl salt)
$R^{5*}$ = $R^5$
W = F.15

Synthesis analogous to Example 20 starting from the compound Example 4.
MS(FAB): 1116.9 $(M+H)^⊕$ Example 22

$R^5$ = $OCOCH_2N(Et)$ $(CH_2)_2NH(Et)$
N-ethyl-N-(2-ethylaminoethyl)-amino-acetoxy (as the HCl salt)
$R^{5*}$ = OH
W = F.15

Synthesis analogous to Example 24 and 23 from the compound Example 1.
MS(FAB): 1287.6 $(M+H)^⊕$ Example 23

$R^5$ = $OCOCH_2N(Et)$ $(CH_2)_2N(Et)COOC(Me)_3$
N-[2(N-tert-butoxycarbonyl-N-ethyl-amino)-ethyl]-N-ethylamino-acetoxy
$R^{5*}$ = $R^5$
W = F.15

157 mg of product were obtained from 216 mg of the compound Example 4 in 5 ml of acetonitrile and 272 mg of N-tert-butoxycarbonyl-N,N'-diethylethylenediamine with a spatula-tip of KI after stirring at RT for 2 days, customary working up and chromatography over silica gel (EA:toluene 7:3).

MS(FAB): [1644.9, 1643.9]$(M+H)^⊕$

Example 24

$R^5$ = $OCOCH_2N(Et)$ $(CH_2)_2NH(Et)$
N-ethyl-N-(2-ethylaminoethyl)-amino-acetoxy (as the HCl salt)
$R^{5*}$ = $R^5$
W = F.15

Synthesis analogous to Example 9 from the compound Example 23. The compound is obtained as the hydrochloride.
MS(FAB): 1443.7 $(M+H)^⊕$ Example 25

$R^5$ = $OCOCH_2NH(CH_2)_3N(Me)$ $(CH_2)_2NH(Me)$
7-methyl-3,7,10-triaza-undecanoyloxy (as the HCl salt)
$R^{5*}$ = OH
W = F.15

218 mg of the compound Example 3 were stirred in 5 ml of acetonitrile with 133 mg of N-(3-aminopropyl)-N'-(tert-butoxycarbonyl)-N,N'-dimethyl-ethylenediamine and a spatula-tip of KI at RT for 24 hours. The solvent was distilled off in vacuo and the residue was taken up in EA. The mixture was extracted by shaking 2× with saturated $KHCO_3$ solution and the organic phase was dried with $Na_2SO_4$ and evaporated in vacuo. Purification was carried out over silica gel (EA:MeOH:triethylamine 90:10:0.2). The target product was evaporated in vacuo 2× with toluene and the residue was then triturated with n-pentane and dried. 146 mg of product were obtained, and were converted into the desired end product by treatment with 6N HCl in dioxane analogously to Example 9. The yield was 102 mg.

MS(FAB): 1316.6 $(M+H)^⊕$ a) Preparation of N-(3-aminopropyl)-N'-(tert-butoxycarbonyl)-N,N'-dimethyl-ethylenediamine 1.9 g of N-(tert-butoxycarbonyl)-N'-(2-cyanoethyl)-N,N'-dimethyl-ethylenediamine (Example 25-b) were dissolved in 100 ml of saturated methanolic ammonia and hydrogenated with 5 g of Raney nickel at RT under 10 atmospheres of $H_2$ for 24 hours. The catalyst was filtered off and washed with MeOH and the filtrate was concentrated in vacuo. The residue was taken up in toluene, insoluble material was filtered off, the filtrate was concentrated in vacuo and the residue was dried. 1.93 g of product were obtained.

MS(Cl): 246 $(M+H)^⊕$, 190, 146 b) Preparation of N-(tert-butoxycarbonyl)-N'-(2-cyanoethyl)-N,N'-dimethyl-ethylenediamine 530 mg of acrylonitrile were slowly added to 1.88 g of N-(tert-butoxycarbonyl)-N,N'-dimethyl-ethylenediamine, while cooling with ice. The mixture was stirred at 0° C. for 1 hour, at RT for 14 hours and at 60° C. for 2 hours. The volatile constituents were removed in vacuo and the residue was purified by chromatography over silica gel (EA:MeOH 9:1). 1.92 g of product were obtained. MS(Cl): 242 $(M+H)^⊕$, 186, 142

Example 26

R$^5$ = OCOCH$_2$NH(CH$_2$)$_3$N(Me) (CH$_2$)$_2$NH(Me)
   7-methyl-3,7,10-triaza-undecanoyloxy
R$^{5*}$ = R$^5$
W = F.15

Preparation analogous to Example 25 from the compound Example 3.
MS(FAB): 1501.8 (M+H)$^\oplus$

Example 27

R$^5$ = OCOCH$_2$N[CH$_2$CONHCH$_2$(CHOH)$_4$CH$_2$OH]$_2$
   bis-(2S,3R,4R,5R,6-pentahydroxyhexyl-amino-
   carbonylmethyl)-amino-acetoxy
R$^{5*}$ = OH
W = F.15

Synthesis analogous to Example 18/19 from the compound Example 3 and iminodiacetic acid bis-(2S,3R,4R,5R, 6-pentahydroxyhexylamide) and with N-ethyl-diisopropylamine and KI. Chromatography over silica gel (first EA:MeOH 95:5 to 70:30, then EA:MeOH:H$_2$O 50:50:2)
MS(FAB): 1653 (M+H)$^\oplus$ a) Preparation of imino-diacetic acid bis-(2S,3R,4R,5R,6-pentahydroxyhexylamide)

1.33 g of N-ethyl-diisopropylamine, 832 mg of D-glucamine, 653 mg of α-hydroxyliminocyanoacetic acid ethyl ester and 1.5 g of TOTU in 20 ml of absolute DMF were added to 560 mg of N-carbobenzoxycarbonyl-protected iminodiacetic acid, while cooling with ice. The mixture was stirred at RT for 2 hours. The solvent was removed in vacuo and the residue was purified over silica gel (DCM:MeOH:H$_2$O 40:10:1 to 25:25:1). 745 mg of product were obtained.
MS(FAB): 594 (M+H)$^\oplus$ 730 mg of the product were dissolved in 50 ml of warm MeOH, the solution was cooled to RT and the product was hydrogenated with a spatula-tip of Pd (5% on charcoal). The pH was kept at 5–6 with 0.5N HCl in MeOH. After 0.5 hour, a few ml of water were added and hydrogenation was continued for 2 hours. The catalyst was filtered off with suction and rinsed with water. The organic solvent was evaporated off in vacuo and the aqueous residue was freeze-dried. 570 mg of the desired product were obtained.

NMR(200 MHz, DMSO<D6>): 3.00–3.09 (m, 2H); 3.10–3.35 (m, about 19H); 4.18 (m, 6H); 4.25 (m, 2H); 4.41 (d, 4 Hz, 2H); 8.13 (t, 4 Hz, 2H).
MS(FAB): 460 (M+H)$^\oplus$

Example 28

R$^5$ = OCOCH$_2$N[CH$_2$CONHCH$_2$(CHOH)$_4$CH$_2$OH]$_2$
   bis-(2S,3R,4R,5R,6-pentahydroxyhexyl-amino-
   carbonylmethyl)-amino-acetoxy
R$^{5*}$ = R$^5$
W = F.15

Synthesis analogous to Example 27 from the compound Example 4. Chromatography over silica gel (EA:MeOH:H$_2$O 90:10:1 to 50:50:2).
MS(FAB): 2153 (M+Na)$^\oplus$, 2131 (M+H)$^\oplus$

Example 29

R$^5$ = OCOC(Me)$_2$NH(CH$_2$)$_2$N(Me)$_2$
   a-[2-(dimethylamino)-ethyl-amino]-isobutyryloxy
R$^{5*}$ = OH
W = F.15

Synthesis from compound Example 3 and N,N-dimethylethyl-enediamine in acetonitrile (8 hours, 50° C.), purification by chromatography over silica gel (EA:MeOH 9:1, 1% of triethylamine)
MS(FAB): 1287.7 (M+H)$^\oplus$; 1197.7

Example 30

R$^5$ = OCOCH$_2$NHCH$_2$CONHCH$_2$[CH(OH)]$_4$CH$_2$OH
   (2S,3R,4R,5R,6-pentahydroxyhexyl-aminocarbonyl-
   methylamino)-acetoxy
R$^{5*}$ = OH
W = F.15

125 mg of the compound Example 1 were dissolved in 1.5 ml of absolute DMF, and a solution of 48 mg of imino-diacetic acid bis-(2S,3R,4R,5R,6-pentahydroxyhexylamide) (Example 26-a) in 1.5 ml of absolute DMF was added. 52 mg of N-ethyl-diisopropylamine and a spatula-tip of KI were added to the reaction mixture. The mixture was stirred at RT for 4 hours and then at 50° C. for 3 hours. The reaction solution was concentrated in vacuo, the residue was taken up in DCM and the mixture was extracted with aqueous KHSO$_4$ solution. The organic phase was dried with MgSO$_4$ and the solvent was removed in vacuo. Purification was carried out over silica gel (toluene:EA 1:1 to 1:10). 37 mg of product were obtained.
MS(FAB): 1431.7 (M+Na)$^\oplus$, 1409.7 (M+H)$^\oplus$ a) Preparation of glycine (2S,3R,4R,5R,6-pentahydroxyhexyl)-amide A spatula-tip of Pd (5% on charcoal) was added to 820 mg of the compound Example 30-b in 50 ml of MeOH at RT. The pH was brought to pH 3–4 with a 5N HCl in MeOH and hydrogenation was carried out at RT for 4 hours. The catalyst was filtered off with suction and washed with MeOH and the filtrate was dried with MgSO$_4$ and concentrated in vacuo. 600 mg of product were obtained.
MS(FAB): 261.2 (M+Na)$^\oplus$, 239.3 (M+H)$^\oplus$ b) Preparation of N-Z-glycine (2S,3R,4R,5R,6-pentahydroxyhexyl)-amide 1.6 g of TBTU and 675 mg of HOBT were added to 1.05 g of N-Z-glycine and 906 mg of D-glucamine in 15 ml of absolute DMF. 2.59 g of N-ethyl-diisopropylamine were added to the reaction solution, while cooling with ice. The mixture was allowed to warm to RT and was stirred at RT for 1 hour. The solvent was distilled off in vacuo and the residue was dissolved in water. The solution was diluted with acetone and the unreacted glucamine which had precipitated out was filtered off with suction. The mother liquor was concentrated in vacuo and the water/acetone operation was repeated. The filtrate was concentrated in vacuo and the residue was evaporated 2× with toluene and then dried in a desiccator. 840 mg of product were obtained.
MS(FAB) : 395.2 (M+Na)$^\oplus$, 373.2 (M+H)$^\oplus$

Example 31

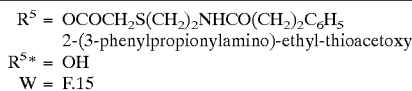

R⁵ = OCOCH₂S(CH₂)₂NHCO(CH₂)₂C₆H₅
  2-(3-phenylpropionylamino)-ethyl-thioacetoxy
R⁵* = OH
W = F.15

125 mg of the compound Example 1, 42 mg of 2-(3-phenylpropionylamino)-ethyl-thiol (Example 30-a) and 26 mg of N-ethyl-diisopropylamine were stirred in 2.5 ml of dry THF at RT for 3 days. The solvent was removed in vacuo, the residue was taken up in EA, the mixture was extracted with NaCl solution (3×) and the organic phase was dried and concentrated in vacuo. Chromatography over silica gel (DCM:MeOH 97:3) gave the desired product, which was also washed with ether.

Yield: 131 mg MS(FAB): 1380.6 (M+H)⊕, 1362.5 a) Preparation of 2-(3-phenylpropionylamino)-ethylthiol 6.75 g of 3-phenylpropionyl chloride in 10 ml of DCM were added dropwise to a solution of 5.68 g of 2-mercaptoethylamine hydrochloride and 10.12 g of triethylamine in 200 ml of DCM at 0° C. When the addition had ended, the mixture was subsequently stirred at 0° C. for a further 40 minutes. The reaction mixture was washed successively with water, 0.4N HCl and then again with water, dried over Na₂SO₄ and concentrated in vacuo. The residue was purified over silica gel (toluene:EA 7:3). Yield: 6.2 g Melting point: 59°–61° C.

MS(Dl): 210 (M+H)⊕

Example 32

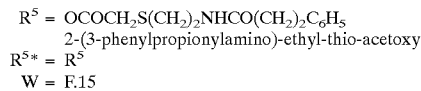

R⁵ = OCOCH₂S(CH₂)₂NHCO(CH₂)₂C₆H₅
  2-(3-phenylpropionylamino)-ethyl-thio-acetoxy
R⁵* = R⁵
W = F.15

Synthesis analogous to Example 31 from the compound Example 4.

MS(FAB): 1629.7 (M+H)⊕

Example 33

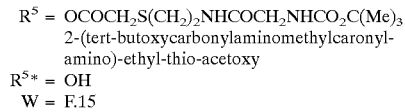

R⁵ = OCOCH₂S(CH₂)₂NHCOCH₂NHCO₂C(Me)₃
  2-(tert-butoxycarbonylaminomethylcaronyl-amino)-ethyl-thio-acetoxy
R⁵* = OH
W = F.15

Synthesis analogous to Example 31 from the compounds Example 1 and Example 33-b.

MS(FAB): 1405.7 (M+H)⊕, 1387.6, 1305.7 a) Preparation of bis-[2-(tert-butoxycarbonylaminomethylcarbonylamino)-ethane] disulfide 4.14 g of N-ethyl-diisopropylamine were added dropwise to 0.9 g of cystamine dihydrochloride, 2.1 g of N-tert-butoxycarbonylglycine, 1.62 g of HOBT and 3.85 g of TBTU in 50 ml of absolute DMF at 10°–15° C. in the course of 5 minutes. When the addition had ended, the mixture was stirred at RT for a further 2 hours. The solvent was evaporated off in vacuo, the residue was dissolved in EA and the solution was washed 2× with saturated NaHCO₃ solution and then with NaCl solution, dried over Na₂SO₄, filtered and concentrated in vacuo. The residue was purified over silica gel (EA:MeOH 99:1 to 95:5).

Yield: 1.8 g MS(Dl): 467 (M+H)⊕, 367, 267 b) Preparation of 2-(tert-butoxycarbonylaminomethylcarbonylamino)-ethyl-thiol 0.33 g of NaBH₄ was added in portions to 1.0 g of bis-[2-(tert-butoxycarbonylaminomethylcarbonylamino)-ethane] disulfide (Example 33-a) in 35 ml of MeOH, while cooling with ice. When the addition had ended, the mixture was subsequently stirred at 0° C. for a further 30 minutes and then at RT for 30 minutes. The reaction mixture was concentrated in vacuo and the residue was taken up in EA. The pH was cautiously brought to 3 by addition of 0.1N HCl, the mixture was stirred for 15 minutes, the phases were separated and the organic phase was washed 2× with NaCl solution, dried over Na₂SO₄, filtered and concentrated in vacuo. The residue was purified over silica gel (EA:MeOH 96:4).

Yield: 0.8 g MS(Cl): 235 (M+H)⊕, 135

Example 34

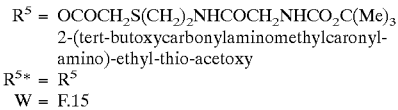

R⁵ = OCOCH₂S(CH₂)₂NHCOCH₂NHCO₂C(Me)₃
  2-(tert-butoxycarbonylaminomethylcaronyl-amino)-ethyl-thio-acetoxy
R⁵* = R⁵
W = F.15

Synthesis analogous to Example 33 from the compounds Example 4 and 33-a.

MS(FAB): 1679.7 (M+H)⊕, 1580.0, 1479.9

Example 35

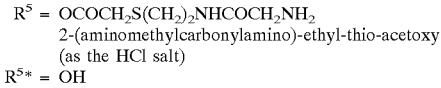

R⁵ = OCOCH₂S(CH₂)₂NHCOCH₂NH₂
  2-(aminomethylcarbonylamino)-ethyl-thio-acetoxy
  (as the HCl salt)
R⁵* = OH Synthesis from the compound Example 33 analogously to Example 9.

MS(FAB): 1305.7 (M+H)⊕

Example 36

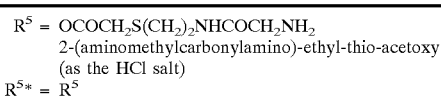

R⁵ = OCOCH₂S(CH₂)₂NHCOCH₂NH₂
  2-(aminomethylcarbonylamino)-ethyl-thio-acetoxy
  (as the HCl salt)
R⁵* = R⁵

Synthesis from the compound Example 34 analogously to Example 9.

MS(FAB): 1479.9 (M+H)⊕

Example 37

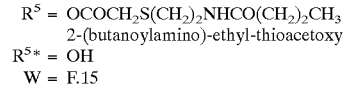

R⁵ = OCOCH₂S(CH₂)₂NHCO(CH₂)₂CH₃
  2-(butanoylamino)-ethyl-thioacetoxy
R⁵* = OH
W = F.15

Synthesis analogous to Example 31 from the compounds Example 1 and Example 37-a

MS(FAB): 1340.7 (M+Na)⊕, 1318 (M+H)⊕, 1300.6 a) Preparation of 2-(butanoylamino)-ethyl-thiol 4.26 g of butyryl chloride in 10 ml of DSM were added dropwise to a solution of 5.68 g of 2-mercaptoethylamine hydrochloride and 10.12 g of triethylamine in 200 ml of DSM at 0° C. When the addition had ended, the mixture was subsequently stirred at 0° C. for a further 40 minutes. The reaction mixture was washed successively with water, 0.4N HCl and then again with water, dried over $Na_2SO_4$ and concentrated in vacuo. The residue was purified over silica gel (toluene:EA 7:3).

Yield: 4.1 g MS(DI): 148 (M+H)⊕

Example 38

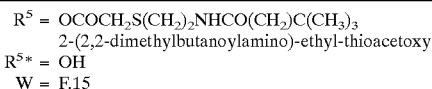

$R^5$ = $OCOCH_2S(CH_2)_2NHCO(CH_2)C(CH_3)_3$
2-(2,2-dimethylbutanoylamino)-ethyl-thioacetoxy
$R^{5*}$ = OH
W = F.15

Synthesis analogous to Example 31 from the compounds Example 1 and Example 38-a.

MS(FAB): 1368.7 (M+Na)⊕, 1346 (M+H)⊕, 1328.7 a) Preparation of 2-(2,2-dimethylbutanoylamino)-ethylthiol 5.39 g of dimethylbutyryl chloride in 10 ml of DSM were added dropwise to a solution of 5.68 g of 2-mercaptoethylamine hydrochloride and 10.12 g of triethylamine in 200 ml of DSM at 0° C. in the course of 20 minutes. When the addition had ended, the mixture was subsequently stirred at 0° C. for a further 40 minutes. The reaction mixture was washed successively with water, 0.4N HCl and then again with water, dried over $Na_2SO_4$ and concentrated in vacuo. The residue was purified over silica gel (toluene:EA 7:3).

Yield: 4.5 g MS(DI): 176 (M+H)⊕

Example 39

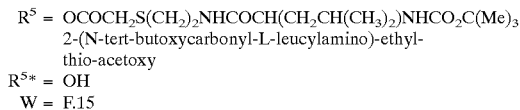

$R^5$ = $OCOCH_2S(CH_2)_2NHCOCH(CH_2CH(CH_3)_2)NHCO_2C(Me)_3$
2-(N-tert-butoxycarbonyl-L-leucylamino)-ethyl-thio-acetoxy
$R^{5*}$ = OH
W = F.15

Synthesis analogous to Example 31 from the compounds Example 1 and Example 39-b.

MS(FAB): 1484.2 (M+Na)⊕, 2462.2 (M+H)⊕, 1444.2, 1362.0 a) Preparation of bis-[2-(N-tert-butoxycarbonyl-L-leucylamino)ethane] disulfide

Synthesis analogous to Example 33-a from cystamine dihydrochloride and N-tert-butoxycarbonyl-L-leucine.

MS(DI) : 579 (M+H)⊕, 479, 379 b) Preparation of 2-(N-tert-butoxycarbonyl-L-leucylamino)-ethyl-thiol

Synthesis analogous to Example 33-b from 39-a.

MS(CI): 291 (M+H)⊕, 191

Example 40

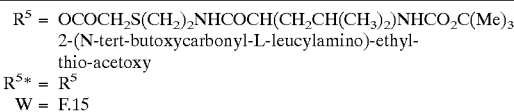

$R^5$ = $OCOCH_2S(CH_2)_2NHCOCH(CH_2CH(CH_3)_2)NHCO_2C(Me)_3$
2-(N-tert-butoxycarbonyl-L-leucylamino)-ethyl-thio-acetoxy
$R^{5*}$ = $R^5$
W = F.15

Synthesis analogous to Example 33 from the compounds Example 1 and Example 39-b.

MS(FAB): 1815 (M+Na)⊕, 1792 (M+H)⊕, 1692, 1592

Example 41

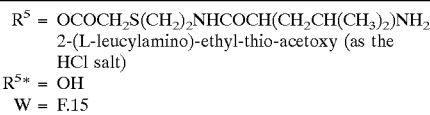

$R^5$ = $OCOCH_2S(CH_2)_2NHCOCH(CH_2CH(CH_3)_2)NH_2$
2-(L-leucylamino)-ethyl-thio-acetoxy (as the HCl salt)
$R^{5*}$ = OH
W = F.15

Synthesis from the compound Example 39 analogously to Example 9.

MS(FAB): 1361.7 (M+H)⊕

Example 42

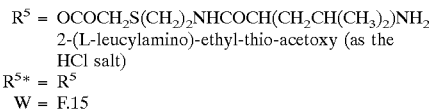

$R^5$ = $OCOCH_2S(CH_2)_2NHCOCH(CH_2CH(CH_3)_2)NH_2$
2-(L-leucylamino)-ethyl-thio-acetoxy (as the HCl salt)
$R^{5*}$ = $R^5$
W = F.15

Synthesis from the compound Example 40 analogously to Example 9.

MS(FAB): 1592.2 (M+H)⊕

Example 43

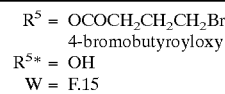

$R^5$ = $OCOCH_2CH_2CH_2Br$
4-bromobutyroyloxy
$R^{5*}$ = OH
W = F.15

1.13 g (1 mmol) of N,N'-bis[(2S-(1,1-dimethylethylsulfonylmethyl)-3-(1-naphthyl)-propionyl)-L-valyl]-2S,5S-diamino-1,6-diphenyl-hexane-3R,4R-diol ($R^5$=$R^{5*}$=OH) were dissolved in 5 ml of absolute THF, and 0.46 ml (4 mmol) of 4-bromobutyryl chloride was added. The mixture was then stirred at RT for 12 hours. The reaction solution was diluted with 100 ml of ethyl acetate and extracted several times with water and saturated sodium chloride solution. The organic phase was dried with sodium sulfate, filtered and evaporated to dryness in vacuo. 640 mg of an amorphous product remained.

MS: 1279.5 (M+H)⊕

Example 44

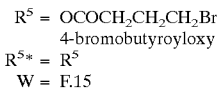

800 mg of N,N'-bis[(2S-(1,1-dimethylethylsulfonylmethyl)-3-(1-naphthyl)-propionyl)-L-valyl]-2S, 5S-diamino-1,6-diphenyl-hexane-3R,4R-diol ($R^5=R^{5*}=OH$) and 864 mg of DMAP were dissolved together in 20 ml of absolute THF, and 0.2 ml of 4-bromobutyryl chloride is added. The mixture was stirred at RT for 18 hours. It was then diluted with ethyl acetate and extracted several times with 10% strength citric acid solution and saturated sodium chloride solution. The organic phase was dried over sodium sulfate, filtered and concentrated to dryness in vacuo. 570 mg of an amorphous product remained.

MS: 1429.5 $(M+H)^\oplus$

Example 45

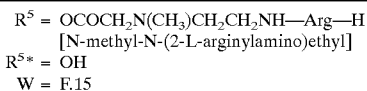

205 mg of the compound from Example 45g were dissolved in 1 ml of methylene chloride, 5 ml of trifluoroacetic acid and 0.45 ml of m-cresol. 0.48 ml of trimethylsilyl bromide was then added and the mixture was stirred at RT for 2 hours. The reaction solution was added to 100 ml of tert-butyl methyl ether and the reaction product was isolated by centrifugation. After drying, 160 mg of the title compound remained as the trihydrobromide.

MS: 1403 (M+H)

Example 45a
Z—N(CH$_3$)—CH$_2$CH$_2$—OH  N-benzyloxycarbonyl-2-methylamino-ethanol 4.5 g (0.06 mol) of 2-methylamino-ethanol are dissolved in 50 ml of absolute tetrahydrofuran, and a solution of 14.9 g (0.06 mol) of N-(benzyloxycarbonyloxy)-succinimide in 30 ml of THF is added, with gentle cooling. The mixture is then stirred at RT for 4 hours. The reaction solution is concentrated on a rotary evaporator in vacuo and the residue which remains is taken up in 100 ml of ethyl acetate. The organic phase is washed several times with 10% strength citric acid solution and 10% potassium bicarbonate solution and saturated NaCl solution. It is dried with sodium sulfate and filtered and the filtrate is concentrated to dryness on a rotary evaporator. A colorless oil remains.

Yield: 11.4 g MS: 210 (M+H)

Example 45b
Z—N(CH$_3$)—CH$_2$CH$_2$—OTos  N-benzyloxycarbonyl-2-methylamino-1-p-tosyloxy-ethane 11.3 g (0.054 mol) of N-Z-methylamino-ethanol (compound from Example 45a) are dissolved in 100 ml of pyridine and the solution is cooled to 0° C. A solution of 12.2 g (0.064 mol) of 4-toluene-sulfonyl chloride in 60 ml of chloroform is added dropwise in the course of 30 minutes and the mixture is stirred overnight at 0° C. The reaction solution is then concentrated on a rotary evaporator, the residue is taken up in 200 ml of ethyl acetate, the mixture is washed several times with 10% strength citric acid solution and saturated sodium chloride solution, dried with sodium sulfate and filtered and the filtrate is concentrated on a rotary evaporator in vacuo. The crude product which remains is purified by chromatography over silica gel (methyl tert-butyl ether/cyclohexane:3/1).

Yield: 13 g MS: 364 (M+H)

Example 45c
Z—N(CH$_3$)—CH$_2$CH$_2$—N$_3$  N-benzyloxycarbonyl-2-methylamino-ethylazide 4.7 g (0.013 mol) of the compound from Example 45b are heated together with 2.5 g (0.039 mol) of sodium azide and 1 g of crown ether 18-crown-6 at 70° C. in 100 ml of absolute dimethylformamide for 1 hour. The mixture is then concentrated on a rotary evaporator in vacuo, the residue is taken up in 150 ml of ethyl acetate and the mixture is washed several times with 10% strength citric acid solution, 10% strength KHCO$_3$ solution and saturated sodium chloride solution. It is dried with sodium sulfate and filtered and the filtrate is concentrated on a rotary evaporator in vacuo. A yellowish, readily mobile liquid remains.

Yield: 2.7 g MS: 235 (M+H)

Example 45d
Z—N(CH$_3$)—CH$_2$CH$_2$—NH$_2$*HCl  2-(N-benzyloxycarbonyl-N-methyl-amino)-ethylamine hydrochloride 2.1 g (9 mmol) of azide from Example 45c are dissolved in 50 ml of methanol, and 6 g (27 mmol) of tin(II) chloride dihydrate are added. The mixture is stirred at RT for 2 hours (evolution of N$_2$ has ended) and concentrated to dryness in vacuo. The residue is taken up in a little water and the mixture is brought to pH 11 with 2M NaOH. The alkaline solution is extracted 3× with 100 ml of methyl tert-butyl ether and the combined organic phases are washed 2× with saturated sodium chloride solution. The organic phase is dried with sodium sulfate, filtered and concentrated on a rotary evaporator in vacuo. The oil which remains is dissolved in 100 ml of diethyl ether, and 1M of ethereal HCl is added to precipitate the hydrochloride. The precipitate is filtered off with suction, washed thoroughly with ether and dried in a desiccator.

Yield: 2 g MS: 209 (M+H)

Example 45e
Boc-Arg(Mtr)—NH—CH$_2$CH$_2$—N(CH$_3$)—Z  N-[N$_\alpha$-tert-butyloxycarbonyl-N$_\omega$-(4-methoxy-2,3,6-tri-methylbenzenesulfonyl)-L-arginyl]-N'-[benzyloxycarbonyl-N'-methylethylenediamine 2.43 g (5 mmol) of Boc-Arg(Mtr)—OH, 675 mg (5 mmol) of N-hydroxybenzotriazole and 1.22 g (5 mmol) of 2-(N-benzyloxycarbonyl-N-methyl-amino)-ethylamine hydrochloride [45d] are dissolved together in 25 ml of dimethylformamide, and 1.13 g (S.5 mmol) of N,N'-dicyclo-hexylcarbodiimide and 0.85 ml (5 mmol) of diisopropyl-ethylamine are added at 0° C. The solution is stirred at 0° C. for 20 minutes and at RT for 3 hours. The precipitate is filtered off and the filtrate is concentrated on a rotary evaporator in vacuo. The residue is taken up in ethyl acetate and the mixture is washed several times with 10% strength citric acid solution, 10% strength KHCO$_3$ solution and saturated NaCl solution. It is dried with sodium sulfate and filtered and the filtrate is evaporated in vacuo.

Yield: 2.4 g of amorphous product MS: 677.3 (M+H)

Example 45f
Boc-Arg(Mtr)—NH—CH$_2$CH$_2$N(CH$_3$)—H  N-[N$_\alpha$-tert-butyloxycarbonyl-N$_\omega$-(4-methoxy-2,3,6-tri-methylbenzenesulfonyl)-L-arginyl] -N'-methyl-ethylene-diamine 2.1 g of the compound from Example 45e are dissolved in 30 ml of tetrahydrofuran and hydrogenated with 400 mg of catalyst (10% of Pd/C) at RT for 4 hours. The catalyst is filtered off and the filtrate is evaporated to dryness in vacuo.
Yield: 1.4 g of amorphous product MS: 544 (M+H)

Example 45g $R^5$ = OCOCH$_2$N(CH$_3$)CH$_2$CH$_2$NH—Arg-(Mtr)-Boc
{N-methyl-N-[2-(N$_\alpha$-tert-butyloxycarbonyl-[N$_\omega$-(4-methoxy-2,3,6-trimethylbenzenesulfonyl)-L-arginyl]-N-aminoethyl]amno}-acetoxy
$R^{5*}$ = OH
W = F.15

250.4 mg (0.2 mmol) of compound from Example 1 are dissolved together with (0.4 mmol) 217.1 mg of the compound from Example 45f and a catalytic amount of 10 mg of potassium iodide in 2 ml of acetonitrile and the mixture is stirred at RT for 12 hours. After the solvent has been evaporated off, the crude product is purified by chromatography on silica gel. (Methylene chloride/methanol: 15/1)
MS: 1715 (M+H)

Example 46

$R^5$ = OCOCH$_2$N(CH$_3$)CH$_2$CH$_2$NH—Arg—H
[N-methyl-N-(2-L-arginyl)-aminoethyl)amino]-acetyloxy
$R^{5*}$ = $R^5$
W = F.15

The protective groups are split off from 46a by a method analogous to that described in Example 45.
MS: 1673 (M+H)

Example 46a
$R^5$=OCOCH$_2$N(CH$_3$)CH$_2$CH$_2$NH-Arg-(Mtr)-Boc
$R^{5*}$=$R^5$
W=F.15

274 mg (0.2 mmol) of the compound from Example 2 are dissolved together with 434 mg (0.8 mmol) of the compound from Example 45f and a catalytic amount of 20 mg of potassium iodide in 3 ml of acetonitrile and the solution is stirred at RT for 24 hours. After the solvent has been removed, the crude product is purified by chromatography over silica gel. (Methylene chloride/methanol: 12/1)
Yield: 330 mg MS: 2297 (M+H)

Example 47

$R^5$ = OCOCH$_2$N(CH$_3$)CH$_2$CH$_2$NH—Gly—H
[N-methyl-N-(2-glycyl)-aminoethyl)amino]-acetyloxy
$R^{5*}$ = OH
W = F.15

The protective groups are split off from 47c by a method analogous to that described in Example 45.
MS: 1302.7 (M+H)

Example 47a
Boc-Gly-NH—CH$_2$CH$_2$N(CH$_3$)—Z N-Benzyloxycarbonyl-[N-methyl-N-(tert-butyloxycarbonyl-glycyl-aminoethyl)] amine The synthesis is carried out by a method analogous to that described in Example 45e from Boc-Gly-OH and the compound from Example 45d.
MS: 366 (M+H)

Example 47b
Boc-Gly-NH—CH$_2$CH$_2$N(CH$_3$)—H [N-methyl-N-(tert-butyloxycarbonyl-glycyl-aminoethyl)]-amine The synthesis is carried out by a method analogous to that described in Example 45f from 47a and hydrogen.
MS: 252 (M+H)

Example 47c $R^5$ = OCOCH$_2$N(CH$_3$)—CH$_2$CH$_2$NH—Gly—Boc
[N-methyl-N-{2-(N-tert-butyloxycarbonyl-glycyl)-aminoethyl}-amino]acetyloxy
$R^{5*}$ = OH
W = F.15

The synthesis is carried out by a method analogous to that described in Example 45g from 47b and the compound from Example 1.
MS: 1402.8 (M+H)

Example 48

$R^5$ = OCOCH$_2$N(CH$_3$)CH$_2$CH$_2$NH—Gly—H
[N-methyl-N-(2-glycyl-aminoethyl)amino]-acetyloxy
$R^{5*}$ = $R^5$
W = F.15

The protective groups are split off from 48a by a method analogous to that described in Example 45.
MS: 1445 (M+H)

Example 48a $R^5$ = OCOCH$_2$N(CH$_3$)CH$_2$CH$_2$NH—Gly—Boc
[N-methyl-N-(2-tert-butyloxycarbonyl-glycyl-aminoethyl)amino]acetyloxy
$R^{5*}$ = $R^5$
W = F.15

The synthesis is carried out by a method analogous to that described in Example 46a from 47b and the compound from Example 2.
MS: 1674 (M+H)

Example 49

$R^5$ = OCOCH$_2$N(CH$_3$)CH$_2$CH$_2$NH—Sar—H
[N-methyl-N-(2-sarcosyl-aminoethyl)amino]-acetyloxy
$R^{5*}$ = $R^5$
W = F.15

The protective groups are split off from 49c by a method analogous to that described in Example 45.
$C_{72}H_{97}N_7O_{12}S_2$ M: 1316.7 MS: 1316.7 (M+H)

Example 49a
Boc-Sar-NH—CH$_2$CH$_2$N(CH$_3$)—Z N-benzyloxycarbonyl-[N-methyl-N-(tert-butyloxycarbonyl-sarcosyl-aminoethyl)] amine The synthesis is carried out by a method analogous to that described in Example 45e from Boc-Sar-OH and the compound from Example 45d.

MS: 380 (M+H)

Example 49b
Boc-Sar-NH—CH₂CH₂N(CH₃)—H [N-methyl-N-tert-butyloxycarbonyl-sarcosyl-aminoethyl)]-amine The synthesis is carried out by a method analogous to that described in Example 45f from 49a and hydrogen.

MS: 246 (M+H)

Example 49c

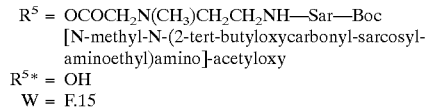

The synthesis is carried out by a method analogous to that described in Example 45g from 49b and the compound from Example 1.

MS: 1416.7 (M+H)

Example 50

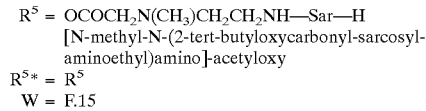

The protective groups are split off from 50a and the compound from Example 2 by a method analogous to that described in Example 45.

MS: 1503 (M+H)

Example 50a

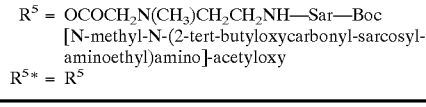

The synthesis is carried out by a method analogous to that described in Example 46a from 49b and the compound from Example 2.

MS: 1702.6 (M+H)

Example 51

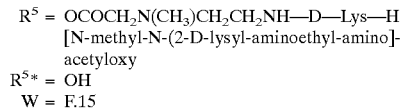

The protective groups are split off from 51c by a method analogous to that described in Example 45.

MS: 1373.4 (M+H)

Example 51a Boc-D-Lys (Boc)—NH—CH₂CH₂N(CH₃)—Z

The synthesis is carried out by a method analogous to that described in Example 45e from Boc-D-Lys(Boc)—OH and the compound from Example 45d.

MS: 538 (M+H)

Example 51b Boc-D-Lys (Boc)—NH—CH₂CH₂N(CH₃)—H

The synthesis is carried out by a method analogous to that described in Example 45f from 51a and hydrogen.

MS: 403 (M+H)

Example 51c

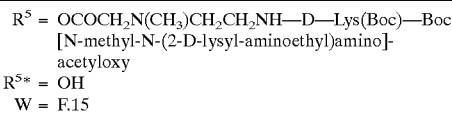

The synthesis is carried out by a method analogous to that described in Example 45g from 51b and the compound from Example 1. MS: 1573 (M+H)

Example 52

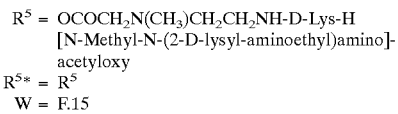

The protective groups are split off from 52a by a method analogous to that described in Example 45.

MS: 1617 (M+H)$^{\oplus}$

Example 52a

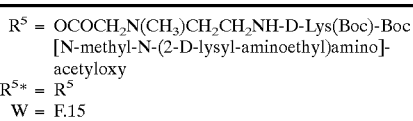

The synthesis is carried out by a method analogous to that described in Example 46a from 51b and the compound from Example 2.

MS: 2017 (M+H)$^{\oplus}$

Example 53

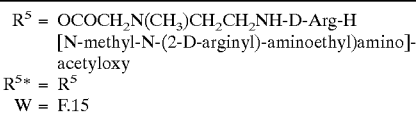

The protective groups are split off from 53c by a method analogous to that described in Example 45.

MS: 1673 (M+H)$^{\oplus}$

Example 53a
Boc-D-Arg(Mtr)—NH—CH₂CH₂N(CH₃)—Z
N-benzyloxycarbonyl-{N-methyl-N-[N$_\alpha$-tert-butyloxycarbon-yl-N$_\omega$-(4-methoxy-2,3,6-trimethyl-benzenesulfonyl)-D-arginyl]-aminoethyl}amine The synthesis is carried out by a method analogous to that described in Example 45e from Boc-D-Arg(Mtr)—OH and the compound from Example 45d.

MS: 678 (M+H)

Example 53b

Boc-D-Arg(Mtr)—NH—CH$_2$CH$_2$N(CH$_3$)—H {N-methyl-N-[N$_\alpha$-tert-butyloxycarbonyl-N$_\omega$-(4-methoxy-2,3,6-trimethylbenzenesulfonyl)-D-arginyl]-aminoethyl}-amine The synthesis is carried out by a method analogous to that described in Example 45f from 53a and hydrogen. MS: 544 (M+H)$^\oplus$

Example 53c

| R$^5$ = OCOCH$_2$N(CH$_3$)CH$_2$CH$_2$NH-D-Arg(Mtr)-Boc {[N-methyl-N-{2-N$_\alpha$-tert-butyloxycarbonyl-N$_\omega$-(4-methoxy-2,3,6-trimethylbenzenesulfonyl)-D-arginyl}-N-aminoethyl]amino}-acetyloxy |
|---|
| R$^{5*}$ = R$^5$ |
| W = F.15 |

The synthesis is carried out by a method analogous to that described in Example 46a from 53b and the compound from Example 2.

MS: 2297 (M+H)$^\oplus$

Example 54

| R$^5$ = OCOCH$_2$N(CH$_3$)CH$_2$CH$_2$NH-Pro-H [N-methyl-N-(2-L-prolyl-aminoethyl)amino]-acetyloxy |
|---|
| R$^{5*}$ = OH |
| W = F.15 |

The protective groups are split off from 48g by a method analogous to that described in Example 39h.

MS: 1344 (M+H)$^\oplus$

Example 54a

Boc-Pro-NH—CH$_2$CH$_2$N—(CH$_3$)—Z
N-benzyloxycarbonyl-[N-methyl-N-(tert-butyloxycarbonyl-L-prolyl-aminoethyl]amine The synthesis is carried out by a method analogous to that described in Example 45e from Boc-Pro-OH and the compound from Example 45d.

MS: 406 (M+H)$^\oplus$

Example 54b

Boc-Pro-NH—CH$_2$CH$_2$N—(CH$_3$)—H

The synthesis is carried out by a method analogous to that described in Example 45f from 54a and hydrogen.

MS: 272 (M+H)$^\oplus$

Example 54c

R$^5$=OCOCH$_2$N(CH$_3$)CH$_2$CH$_2$NH-Pro-Boc
R$^{5*}$=OH
W=F.15

The synthesis is carried out by a method analogous to that described in Example 45g from 54b and the compound from Example 1.

MS: 1442.6 (M+H)$^\oplus$

Example 55

| R$^5$ = OCOCH$_2$N(CH$_3$)CH$_2$CH$_2$NH-Pro-H [N-methyl-N-(2-D-prolyl-aminoethyl)amino]-acetyloxy |
|---|
| R$^{5*}$ = R$^5$ |
| W = F.15 |

The synthesis is carried out by a method analogous to that described in Example 40a from 54b and the compound from Example 2.

MS: 1555 (M+H)$^\oplus$

Example 55a

R$^5$=OCOCH$_2$N(CH$_3$)CH$_2$CH$_2$NH-Pro-Boc
R$^{5*}$=R$^5$
W=F.15

The synthesis is carried out by a method analogous to that described in Example 46a from 54b and the compound from Example 2.

MS: 1754 (M+H)$^\oplus$

Example 56

| R$^5$ = OCOCH$_2$N(CH$_3$)CH$_2$CH$_2$N(CH$_3$)-Arg-D-H [N-methyl-N-(2-D-arginyl-N-2-methyl-aminoethyl)amino]-acetyloxy |
|---|
| R$^{5*}$ = OH |
| W = F.15 |

300 mg of the compound from Example 56d were dissolved in 1 ml of methylene chloride, 5 ml of trifluoroacetic acid and 0.45 ml of m-cresol. 0.48 ml of trimethylsilyl bromide was then added and the mixture was stirred at RT for 2 hours. The reaction solution is added to 100 ml of tert-butyl methyl ether and the reaction product is isolated by centrifugation. After drying, 260 mg of the title compound remain as the trihydrobromide.

MS: 1415.6 (M+H)$^\oplus$

Example 56a Z—N(CH$_3$)—CH$_2$CH$_2$N(CH$_3$)—H N-methyl-(N-benzyloxycarbonyl-2-methylaminoethyl) amine A solution of 18.7 g (0.075 mol) of Z-OSu in 150 ml of THF is added dropwise to 22.8 g (0.25 mol) of N,N'-dimethylethylenediamine in 250 ml of tetrahydrofuran at 0° C. in the course of 30 minutes. After 60 minutes at RT, the precipitate formed (HOSU salt of the educt) is filtered off with suction and washed with THF. The filtrate is concentrated on a rotary evaporator in vacuo. The resulting crude product is purified by chromatography over silica gel. (Methylene chloride/methanol/acetic acid/water: 50/12/2/2). The free base of the desired compound is obtained by neutralization of an aqueous solution of the acetate obtained and extraction with diethyl ether.

Yield: 8.5 g MS: 223 (M+H)$^\oplus$

Example 56b

Boc-D-Arg(Mtr)—N(CH$_3$)—CH$_2$CH$_2$N(CH$_3$)—Z
N-benzyloxycarbonyl-{N-methyl-N-[N$_\alpha$-tert-butyloxycarbonyl-N$_\omega$-(4-methoxy-2,3,6-trimethylbenzenesulfonyl-D-arginyl]-methylaminoethyl}amine The synthesis is carried out by a method analogous to that described in Example 45e from Boc-D-Arg(Mtr)—OH and the compound from Example 56a.

MS: 691.3 (M+H)⊕

Example 56c

Boc-D-Arg(Mtr)—N(CH$_3$)—CH$_2$CH$_2$N(CH$_3$)—H
{N-methyl-N-[N$_\alpha$-tert-butyloxycarbonyl-N$_\omega$-(4-methoxy-2,3,6-trimethyl-benzenesulfonyl)-D-arginyl]-methylaminoethyl}amine The synthesis is carried out by a method analogous to that described in Example 45f from 56b and hydrogen.

MS: 557.3 (M+H)⊕

Example 56d

| |
|---|
| R$^5$ = OCOCH$_2$N(CH$_3$)CH$_2$CH$_2$N(CH$_3$)-D-Arg(Mtr)-Boc {N-methyl-N-[N$_\alpha$-tert-butyloxycarbonyl-[N$_\omega$-(4-methoxy-2,3,6-trimethyl-benzenesulfonyl)-D-arginyl]-N-methylaminoethyl]amino}-acetyloxy |
| R$^{5*}$ = OH |
| W = F.15 |

250.4 mg (0.2 mmol) of the compound from Example 1, (0.4 mmol) 222.6 mg of the compound from Example 56c and a catalytic amount of 10 mg of potassium iodide are dissolved together in 2 ml of acetonitrile and the solution is stirred at RT for 12 hours. After the solvent has been evaporated, the crude product is purified by chromatography over silica gel. (Methylene chloride/methanol: 15/1)

MS: 1728 (M+H)⊕

Example 57

| |
|---|
| R$^5$ = OCOCH$_2$N(CH$_3$)CH$_2$CH$_2$N(CH$_3$)-Gly-H [N-methyl-N-(2-glycyl-N-2-methylaminoethyl)-amino]-acetyloxy |
| R$^{5*}$ = OH |
| W = F.15 |

The protective groups are split off from 57c by a method analogous to that described in Example 45.

MS: 1317.6 (M+H)⊕

Example 57a

Boc-Gly-N(CH$_3$)—CH$_2$CH$_2$N—(CH$_3$)—Z
N-benzyloxycarbonyl-[N-methyl-N-(tert-butyloxycarbonyl-glycyl-methylaminoethyl)]amine The synthesis is carried out by a method analogous to that described in Example 45e from Boc-Gly-OH and the compound from Example 56a.

MS: 380.2 (M+H)⊕

Example 57b

Boc-Gly-N(CH$_3$)—CH$_2$CH$_2$N(CH$_3$)—H [N-methyl-N-(tert-butyloxycarbonyl-glycyl-methylaminoethyl)]amine The synthesis is carried out by a method analogous to that described in Example 45f from 57a and hydrogen.

MS: 246 (M+H)⊕

Example 57c

| |
|---|
| R$^5$ = OCOCH$_2$N(CH$_3$)CH$_2$CH$_2$N(CH$_3$)-Gly-Boc [N-methyl-N-(2-tert-butyloxycarbonyl-glycyl-N-2-methyl-aminoethyl)amino]-acetyloxy |
| R$^{5*}$ = OH |
| W = F.15 |

The synthesis is carried out by a method analogous to that described in Example 45g from 57b and the compound from Example 1.

MS: 1688.2 (M+H)⊕

Example 58

| |
|---|
| R$^5$ = OCOCH$_2$N(CH$_3$)CH$_2$CH$_2$N(CH$_3$)-Gly-H [N-methyl-N-(2-glycyl-N-2-methylaminoethyl)-amino]-acetyloxy |
| R$^{5*}$ = R$^5$ |
| W = F.15 |

The protective groups are split off from 58a by a method analogous to that described in Example 45h.

MS: 1473.7 (M+H)

Example 58a

| |
|---|
| R$^5$ = OCOCH$_2$N(CH$_3$)CH$_2$CH$_2$N(CH$_3$)-Gly-Boc [N-methyl-N-(Boc-glycyl-N-2-methylaminoethyl)-amino]-acetyloxy |
| R$^{5*}$ = R$^5$ |
| W = F.15 |

The synthesis is carried out by a method analogous to that described in Example 46a from 57b and the compound from Example 2.

MS: 1702.6 (M+H)⊕

Example 59

| |
|---|
| R$^5$ = OCOCH$_2$N(CH$_3$)CH$_2$CH$_2$N(CH$_3$)-Sar-H [N-methyl-N-(2-sarcosyl-N-2-methyl-aminoethyl)-amino]-acetyloxy |
| R$^{5*}$ = OH |
| W = F.15 |

The protective groups are split off from 59c by a method analogous to that described in Example 45.

MS: 1330.7 (M+H)⊕

Example 59a

Boc-Sar-N(CH$_3$)—CH$_2$CH$_2$N—(CH$_3$)—Z
N-benzyloxycarbonyl-[N-methyl-N-(tert-butyloxycarbonyl-sarcosyl-methylaminoethyl)]amine The synthesis is carried out by a method analogous to that described in Example 45e from Boc-Sar-OH and the compound from Example 56a.

MS: 394.4 (M+H)⊕

Example 59b

Boc-Sar-N(CH$_3$)—CH$_2$CH$_2$N—(CH$_3$)—H [N-methyl-N-(tert-butyloxycarbonyl-sarcosyl-methylaminoethyl]amine The synthesis is carried out by a method analogous to that described in Example 45f from 59a and hydrogen.

MS 260.2 (M+H)⊕

Example 59c
$R^5$=OCOCH$_2$N(CH$_3$)CH$_2$CH$_2$N(CH$_3$)-Sar-Boc
$R^{5*}$=OH
W=F.15

The synthesis is carried out by a method analogous to that described in Example 39g from 54 and the compound from Example 1. MS: 1431.4 (M+H)⊕

Example 60

| |
|---|
| $R^5$ = OCOCH$_2$N(CH$_3$)CH$_2$CH$_2$N(CH$_3$)-Sar-H [N-methyl-N-(2-sarcosyl-N-2-methyl-aminoethyl)-amino]-acetyloxy |
| $R^{5*}$ = $R^5$ |
| W = F.15 |

The protective groups are split off from 60a by a method analogous to that described in Example 45.
MS: 1531 (M+H)⊕

Example 60a

| |
|---|
| $R^5$ = OCOCH$_2$N(CH$_3$)CH$_2$CH$_2$N(CH$_3$)-Sar-Boc [N-methyl-N-(2-tert-butyloxycarbonyl-sarcosyl-N-2-methylaminoethyl)amino]-acetyloxy |
| $R^{5*}$ = $R^5$ |
| W = F.15 |

The synthesis is carried out by a method analogous to that described in Example 46a from 59b and the compound from Example 2.
MS: 1731 (M+H)⊕

Example 61

| |
|---|
| $R^5$ = OCOCH$_2$N(CH$_3$)CH$_2$CH$_2$N(CH$_3$)-L-Arg-H [N-methyl-N-(2-L-arginyl)-N-(2-methyl-amino-ethyl)amino]-acetyloxy |
| $R^{5*}$ = OH |
| W = F.15 |

The protective groups are split off from 61c by a method analogous to that described in Example 45.
MS: 1415.6 (M+H)⊕

Example 61a
Boc-Arg(Mtr)—N(CH$_3$)—CH$_2$CH$_2$N—(CH$_3$)—Z
N-benzyloxycarbonyl-{N-methyl-N-[N$_α$-tert-butyloxycarbon-yl-N$_ω$-(4-methoxy-2,3,6-trimethyl-benzenesulfonyl)-L-arginyl]-methylaminoethyl}amine
The synthesis is carried out by a method analogous to that described in Example.45e from Boc-Arg(Mtr)—OH and the compound from Example 56a.
MS: 691.3 (M+H)⊕

Example 61b
Boc-Arg(Mtr)—N(CH$_3$)—CH$_2$CH$_2$-N(CE$_3$)—H
{N-methyl-N-[N$_α$-tert-butyloxycarbonyl-N$_ω$-(4-methoxy-2,3,6-trimethylbenzenesullonyl)-L-arginyl]aminoethyl}-amine
The synthesis is carried out by a method analogous to that described in Example 45f from 61a and hydrogen.
MS: 557.3 (M+H)⊕

Example 61c

| |
|---|
| $R^5$ = OCOCH$_2$N(CH$_3$)CH$_2$CH$_2$N(CH$_3$)-L-Arg(Mtr)-Boc {[N-methyl-N-[2-N$_α$-tert-butyloxycarbonyl-N$_ω$-(4-methoxy-2,3,6-trimethylbenzenesulfonyl)-L-arginyl]-N-2-methylaminoethyl]amino}-acetyloxy |
| $R^{5*}$ = OH |
| W = F.15 |

The synthesis is carried out by a method analogous to that described in Example 46a from 61b and the compound from Example 2.
MS: 1729 (M+H)⊕

Example 62

| |
|---|
| $R^5$ = OCOCH$_2$N(CH$_3$)CH$_2$CH$_2$N(CH$_3$)-Arg-H [N-methyl-N-(2-L-arginyl)-N-(2-methyl-amino-ethyl)amino]-acetyloxy |
| $R^{5*}$ = $R^5$ |
| W = F.15 |

The protective groups are split off from 62a by a method analogous to that described in Example 45h
MS: 1700.9 (M+H)⊕

Example 62a
$R^5$ OCOCH$_2$N (CH$_3$) CH$_2$CH$_2$N (CH$_3$)-Arg (Mtr)-Boc $R^{5*}$= $R^5$
W=F.15
The synthesis is carried out by a method analogous to that described in Example 46a from 61b and the compound from Example 2.
MS: 2325 (M+H)⊕

Example 63

| |
|---|
| $R^5$ = OCOCH$_2$N(CH$_{32}$)CH$_2$CH$_2$N(CH$_3$)-Arg-D-H [N-methyl-N-(2-D-arginyl)-N-(2-methyl-amino-ethyl)amino]-acetyloxy |
| $R^{5*}$ = $R^5$ |
| W = F.15 |

The synthesis is carried out by a method analogous to that described in Example 45 from 63a.
MS: 1700.9 (M+H)⊕

Example 63a
$R^5$=OCOCH$_2$N(CH$_3$) CH$_2$CH$_2$N(CH$_3$)-Arg(Mtr)-D-Boc
$R^{5*}$=$R^5$
W=F.15
The synthesis is carried out by a method analogous to that described in Example 46a from 56c and the compound from Example 2. MS: 2325 (M+H)⊕

Example 64

| |
|---|
| $R^5$ = OCOCH$_2$N(CH$_3$)CH$_2$CH$_2$N(CH$_3$)-Lys-H [N-methyl-N-(2-L-lysyl-N-2-methyl-aminoethyl)-amino]-acetyloxy |
| $R^{5*}$ = OH |
| W = F.15 |

The protective groups are split off from 60d by a method analogous to that described in Example 39h.

MS: 1389 (M+H)$^{\oplus}$

Example 64a
Boc-Lys (Boc)—N(CH$_3$)—CH$_2$CH$_2$N—(CH$_3$)—Z
N-benzyloxycarbonyl-[N-methyl-N-(N$_\alpha$,N$_\epsilon$-tert-butyloxy-carbonyl-L-lysyl-methylamino-ethyl)]-amine The synthesis is carried out by a method analogous to that described in Example 45e from Boc-Lys(Boc)—OH and the compound from Example 56a.
MS: 551.3 (M+H)$^{\oplus}$

Example 64b
Boc-Lys (Boc)—N(CH$_3$)—CH$_2$CH$_2$N—(CH$_3$)—H
[N-methyl-N-(N$_\alpha$,N$_\epsilon$-tert-butyloxycarbonyl-L-lysyl-methylaminoethyl)]-amine The synthesis is carried out by a method analogous to that described in Example 45f from 64a and hydrogen.
MS: 417.3 (M+H)$^{\oplus}$

Example 64c
R$^5$=OCOCH$_2$N(CH$_3$)CH$_2$CH$_2$N(CH$_3$)-Lys (Boc)-Boc
R$^{5*}$=OH
W=F.15

The synthesis is carried out by a method analogous to that described in Example 45g from 64b and the compound from Example 1. MS: 1588.9 (M+H)$^{\oplus}$

Example 65

| | |
|---|---|
| R$^5$ = | OCOCH$_2$N(CH$_3$)CH$_2$CH$_2$N(CH$_3$)-Lys-H [N-methyl-N-(2-L-lysyl-N-2-methyl-aminoethyl)-amino]-acetyloxy |
| R$^{5*}$ = | R$^5$ |
| W = | F.15 |

The protective groups are split off from 65a by a method analogous to that described in Example 45.
MS: 1644.2 (M+H)$^{\oplus}$

Example 65a
R$^5$=OCOCH$_2$N(CH$_3$)CH$_2$CH$_2$N(CH$_3$)-Lys (Boc)-Boc
R$^{5*}$=R$^5$
W=F.15

The synthesis is carried out by a method analogous to that described in Example 46a from 64b and the compound from Example 2.
MS: 2045 (M+H)$^{\oplus}$

Example 66
R$^5$=OCOCH$_2$N(CH$_3$)CH$_2$CH$_2$N(CH$_3$)-D-Lys-H
R$^{5*}$=OH
W=F.15

The protective groups are split off from 66c by a method analogous to that described in Example 45.
MS: 1389 (M+H)$^{\oplus}$

Example 66a
Boc-D-Lys (Boc)—N(CH$_3$)—CH$_2$CH$_2$N—(CH$_3$)—Z
N-benzyloxycarbonyl-[N-methyl-N-(N$_\alpha$,N$_\epsilon$-tert-butyloxy-carbonyl-D-lysyl-methylamino-ethyl)]-amine The synthesis is carried out by a method analogous to that described in Example 45e from Boc-D-Lys(Boc)—OH and the compound from Example 56a. MS: 551.3 (M+H)

Example 66b
Boc-D-Lys (Boc)—N(CH$_3$)—H$_2$CH$_2$N—(CH$_3$)—H
[N-methyl-N-(N$_\alpha$,N$_\epsilon$-tert-butyloxycarbonyl-D-lysyl-methyl-aminoethyl)]-amine The synthesis is carried out by a method analogous to that described in Example 45f from 64a and hydrogen.
MS: 417.3 (M+H)$^{\oplus}$

Example 66c
R$^5$=OCOCH$_2$N(CH$_3$)CH$_2$CH$_2$N(CH$_3$)-Lys(Boc)-D-Boc
R$^{5*}$=OH
W=F.15

The synthesis is carried out by a method analogous to that described in Example 45g from 66b and the compound from Example 1.
MS: 1588.9 (M+H)$^{\oplus}$

Example 67
R$^5$=OCOCH$_2$N(CH$_3$)CH$_2$CH$_2$N(CH$_3$)-D-Lys-H
R$^{5*}$=R$^5$
W=F.15

The protective groups are split off from 67a by a method analogous to that described in Example 45.
MS: 1644.2 (M+H)$^{\oplus}$

Example 67a
R$^5$=OCOCH$_2$N(CH$_3$)CH$_2$CH$_2$N(CH$_3$)-D-Lys(Boc)-Boc
R$^{5*}$=R$^5$
W=F.15

The synthesis is carried out by a method analogous to that described in Example 46a from 66b and the compound from Example 2.
MS: 2045 (M+H)$^{\oplus}$

Example 68

| | |
|---|---|
| R$^5$ = | OCOCH$_2$N(CH$_3$)CH$_2$CH$_2$N(CH$_3$)-Pro-H [N-methyl-N-(2-L-prolyl-N-2-methyl-aminoethyl)-amino]-acetyloxy |
| R$^{5*}$ = | OH |
| W = | F.15 |

The protective groups are split off from 68c by a method analogous to that described in Example 45h.
MS: 1358 (M+H)$^{\oplus}$

Example 68a
Boc-Pro-N(CH$_3$)—CH$_2$CH$_2$N—(CH$_3$)—Z
N-benzyloxycarbonyl-[N-methyl-N-tert-butyloxycarbonyl-L-prolyl-methylaminoethyl)]amine The synthesis is carried out by a method analogous to that described in Example 45e from Boc-Pro-OH and the compound from Example 56a.
MS: 420.3 (M+H)$^{\oplus}$

Example 68b
Boc-Pro-N(CH$_3$)—CH$_2$CH$_2$N—(CH$_3$)—H [N-methyl-N-(tert-butyloxycarbonyl-L-prolyl-methylaminoethyl)]amine The synthesis is carried out by a method analogous to that described in Example 45f from 68a and hydrogen.
MS: 286 (M+H)$^{\oplus}$

Example 68c

| | |
|---|---|
| R$^5$ = | OCOCH$_2$N(CH$_3$)CH$_2$CH$_2$N(CH$_3$)-Pro-Boc [N-methyl-N-(2-L-prolyl-N-2-methyl-aminoethyl)-amino]-acetyloxy |
| R$^{5*}$ = | OH |
| W = | F.15 |

The synthesis is carried out by a method analogous to that described in Example 45g from 68b and the compound from Example 1.

MS: 1457.6 (M+H)⊕

Example 69

| |
|---|
| $R^5$ = OCOCH$_2$N(CH$_3$)CH$_2$CH$_2$N(CH$_3$)-D-Pro-H [N-methyl-N-(2-D-prolyl-N-2-methyl-aminoethyl)-amino]-acetyloxy |
| $R^{5*}$ = OH |
| W = F.15 |

The protective groups are split off from 69c by a method analogous to that described in Example 45.
MS: 1357.9 (M+H)⊕

Example 69a
Boc-D-Pro-N(CH$_3$)—CH$_2$CH$_2$N—(CH$_3$)—Z

The synthesis is carried out by a method analogous to that described in Example 45e from Boc-D-Pro-OH and the compound from Example 56a.
MS: 420.2 (M+H)⊕

Example 69b
Boc-D-Pro-N(CH$_3$)—CH$_2$—CH$_2$—N(CH$_3$)—H [N-methyl-N-(tert-butyloxycarbonyl-D-prolyl-methylaminoethyl)]amine The synthesis is carried out by a method analogous to that described in Example 45f from 69a and hydrogen.
MS: 286 (M+H)⊕

Example 69c

| |
|---|
| $R^5$ = OCOCH$_2$N(CH$_3$)CH$_2$CH$_2$N(CH$_3$)-D-Pro-Boc [N-methyl-N-(2-D-prolyl-N-2-methyl-aminoethyl)-amino]-acetyloxy |
| $R^{5*}$ = OH |
| W = F.15 |

The synthesis is carried out by a method analogous to that described in Example 45g from 69b and the compound from Example 1.
MS: 1457.6 (M+H)⊕

Example 70

| |
|---|
| $R^5$ = OCOCH$_2$N(CH$_3$)CH$_2$CH$_2$N(CH$_3$)-His-H [N-methyl-N-(2-L-histidyl-N-2-methyl-aminoethyl)-amino]-acetyloxy |
| $R^{5*}$ = OH |
| W = F.15 |

The protective groups are split off from 70c by a method analogous to that described in Example 45.

Example 70a
Boc-His (Boc)—N(CH$_3$)—CH$_2$CH$_2$N—(CH$_3$)—Z
N-benzyloxycarbonyl-{N-methyl-N-[2-bis-(N$_\alpha$,N$_{im}$-tert-butyloxycarbonyl)-L-histidyl]-N-2-methyl-aminoethyl}amine The synthesis is carried out by a method analogous to that described in Example 45e from Boc-His(Boc)—OH and the compound from Example 56a.
MS: 560.3 (M+H)⊕

Example 70b
Boc-His (Boc)—N(CH$_3$)—CH$_2$CH$_2$N—(CH$_3$)—H {N-methyl-N-[2-bis-(N$_\alpha$,N$_{im}$-tert-butyloxycarbonyl)-L-histidyl]-N-2-methyl-aminoethyl}amine The synthesis is carried out by a method analogous to that described in Example 45f from 70a and hydrogen.
MS: 426.3 (M+H)⊕

Example 70c
$R^5$=OCOCH$_2$N(CH$_3$)CH$_2$CH$_2$N(CH$_3$)-His(Boc)-Boc
$R^{5*}$=OH
W=F.15

The synthesis is carried out by a method analogous to that described in Example 39g from 66c and the compound from Example 1.
MS: 1396.7 (M+H)⊕

Example 71

| |
|---|
| $R^5$ = OCOCH$_2$N(CH$_3$)CH$_2$CH$_2$N(CH$_3$)-Trp-H [N-methyl-N-(2-L-tryptophyl-N-2-methyl-aminoethyl)amino]-acetyloxy |
| $R^{5*}$ = OH |
| W = F.15 |

The protective groups are split off from 71c by a method analogous to that described in Example 45.
MS: 1447 (M+H)⊕

Example 71a
Boc-Trp-N(CH$_3$)—CH$_2$CH$_2$N—(CH$_3$)—Z
N-benzyloxycarbonyl-[N-methyl-N-(tert-butyloxycarbonyl-L-tryptophyl-methylaminoethyl)]amine The synthesis is carried out by a method analogous to that described in Example 45e from Boc-Tro—OH and the compound from Example 56a.
MS: 509.3 (M+H)⊕

Example 71b
Boc-Trp-N(CH$_3$)—CH$_2$CH$_2$N—(CH$_3$)—H [N-methyl-N-(tert-butyloxycarbonyl-L-tryptophyl-methyl-aminoethyl)]amine The synthesis is carried out by a method analogous to that described in Example 45f from 71a and hydrogen.
MS: 375.2 (M+H)⊕

Example 71c

| |
|---|
| $R^5$ = OCOCH$_2$N(CH$_3$)CH$_2$CH$_2$N(CH$_3$)-Trp-Boc [N-methyl-N-(2-tert-butyloxycarbonyl-tryptophyl-N-2-methylaminoethyl)amino]-acetyloxy |
| $R^{5*}$ = OH |
| W = F.15 |

The synthesis is carried out by a method analogous to that described in Example 45g from 71b and the compound from Example 1.
MS: 1447 (M+H)⊕

Example 72

| |
|---|
| $R^5$ = OCOCH$_2$N(CH$_3$)CH$_2$CH$_2$CH$_2$N(CH$_3$)-Arg-H [N-methyl-N-(2-L-arginyl)-N-(2-methyl-amino-propyl)amino]-acetyloxy |
| $R^{5*}$ = OH |
| W = F.15 |

The protective groups are split off from 72d by a method analogous to that described in Example 45h.

MS: 1431 (M+H)$^{\oplus}$

Example 72a

Z—N(CH$_3$)—CH$_2$—CH$_2$—CH$_2$—N—(CH$_3$)—Z

The synthesis is carried out by a method analogous to that described in Example 56a from N-(benzyloxycarbonyl-oxy)-succinimide and N,N'-dimethyl-1,3-propanediamine.

MS: 237 (M+H)$^{\oplus}$

Example 72b

Boc-Arg-(Mtr)—N(CH$_3$)—CH$_2$—CH$_2$—CH$_2$—N—(CH$_3$)—Z

The synthesis is carried out by a method analogous to that described in Example 45e from Boc-Arg(Mtr)—OH and the compound from Example 72a. MS: 706 (M+H)$^{\oplus}$

Example 72c

Boc-Arg(Mtr)—N(CH$_3$)—CH$_2$—CH$_2$—CH$_2$—N—(CH$_3$)—H

The synthesis is carried out by a method analogous to that described in Example 45f from 72b and hydrogen.

MS: 571.3 (M+H)$^{\oplus}$

Example 72d $R^5$=OCOCH$_2$—N(CH$_3$)CH$_2$CH$_2$CH$_2$N(CH$_3$)-Arg(Mtr)-Boc
$R^{5*}$=OH
W=F.15

The synthesis is carried out by a method analogous to that described in Example 45g from 72c and the compound of Example 1.

MS: 1743 (M+H)$^{\oplus}$

Example 73

| | |
|---|---|
| $R^5$ = | OCOCH$_2$N(CH$_3$)CH$_2$CH$_2$CH$_2$N(CH$_3$)-Arg-H [N-methyl-N-(2-L-arginyl)-N-2-methyl-aminopropyl)amino]-acetyloxy |
| $R^{5*}$ = | $R^5$ |
| W = | F.15 |

The protective groups are split off from 73a by a method analogous to that described in Example 45h.

MS: 1729 (M+H)$^{\oplus}$

Example 73a $R^5$=OCOCH$_2$N (CH$_3$) CH$_2$CH$_2$CH$_2$N (CH$_3$)-Arg (Mtr)-Boc
$R^{5*}$=$R^5$
W=F.15

The synthesis is carried out by a method analogous to that described in Example 46a from 72c and the compound from Example 2.

MS: 2352 (M+H)$^{\oplus}$

Example 74

$R^5$=OCOCH$_2$CH$_2$CH$_2$(CH$_3$)CH$_2$CH$_2$N(CH$_3$)—H
$R^{5*}$=OH
W=F.15

The protective groups are split off from 74a by a method analogous to that described in Example 45.

C$_{72}$H$_{98}$N$_6$O$_{11}$S$_2$ M: 1287.9 MS: 1289 (M+H)$^{\oplus}$

Example 74a $R^5$=OCOCH$_2$CH$_2$CH$_2$N(CH$_3$)CH$_2$CH$_2$N(cH$_3$)-Boc
$R^{5*}$=OH
W=F.15

The splitting off occurs from 8a and the compound from 43 by a method analogous to that described in Example 45g.

MS: 1389 (M+H)$^{\oplus}$

Example 75

| | |
|---|---|
| $R^5$ = | OCOCH$_2$CH$_2$CH$_2$N(CH$_3$)CH$_2$CH$_2$N(CH$_3$)—H [N-methyl-N-(2-methyl-aminoethyl)amino]-butyryloxy |
| $R^{5*}$ = | $R^5$ |
| W = | F.15 |

The protective groups are split off from 75a by a method analogous to that described in Example 45h.

MS: 1445 (M+H)$^{\oplus}$

Example 75a

| | |
|---|---|
| $R^5$ = | OCOCH$_2$CH$_2$CH$_2$N(CH$_3$)CH$_2$CH$_2$N(CH$_3$)-Boc [N-methyl-N(N-Boc-methylaminoethyl)amino]-butyryloxy |
| $R^{5*}$ = | $R^5$ |
| W = | F.15 |

The synthesis is carried out by a method analogous to that described in Example 46a from 8a and the compound from Example 44.

MS: 1645 (M+H)$^{\oplus}$

Example 76

$R^5$=OCOCH$_2$—N—[CH$_2$PO(CH$_3$)$_2$]—CH$_2$CH$_2$—N(CH$_3$)—H
$R^{5*}$=OH
W=F.15

230 mg of the product from Example 76d were dissolved in 10 ml of glacial acetic acid/methanol: 2/1 and hydrogenated with 80 mg of catalyst (10% Pd/C) at RT for 40 minutes. The catalyst is filtered off and the filtrate is evaporated to dryness in vacuo. 1110 mg of the title compound remain.

Example 76a

CH$_3$—NH—CH$_2$CH$_2$Br$^*$HBr 2-methylaminoethyl bromide hydrobromide 26.2 g (0.35 mol) of N-methylaminoethanol are dissolved in 200 ml of toluene, the solution is cooled to 0° C. and 27.9 ml (0.36 mol) of thionyl bromide are added in the course of 1 hour. The reaction solution is heated to 60° C. and stirred vigorously for 45 minutes. It is then concentrated on a rotary evaporator in vacuo. The viscous mass which remains is taken up in about 1 l of boiling acetone, active charcoal is added and the mixture is filtered. Thereafter, about 600 ml of diisopropyl ether are added and the mixture is left to stand at 0° C. for crystallization. The precipitate is filtered off with suction, washed thoroughly with diisopropyl ether and dried immediately over KOH in a desiccator.

Yield: 48 g

Example 76b

Z—(CH$_3$)N—CH$_2$CH$_2$Br (N-benzyloxycarbonyl-2-methylaminoethyl) bromide 10.94 g (0.05 mol) of 2-methylaminoethyl bromide hydrobromide are dissolved in 80 ml of acetonitrile, and 12.5 g (0.05 mol) of Z-OSu and 6.9 ml (0.05 mol) of triethylamine are added. The mixture is stirred at RT for 45 minutes and concentrated in a rotary evaporator in vacuo and the residue in the flask is taken up in 150 ml of ethyl acetate. The mixture is then washed several times with 10% strength citric acid solution and saturated sodium chloride solution, dried with sodium sulfate and filtered and the filtrate is concentrated to dryness in vacuo. The crude product is purified by chromatography over silica gel. (n-Heptane/ethyl acetate: 5/1)
Yield: 7.8 g MS: 272 (M+H)$^\oplus$ Example 76c
Z—(CH$_3$)N—CH$_2$CH$_2$—NH—CH$_2$PO(CH$_3$)$_2$
N-dimethyloxophosphorylmethyl-(N-benzyloxycarbonyl-2-methylaminoethyl)amine 2.7 g (10 mmol) of (N-benzyloxycarbonyl-2-methylamino)-ethyl bromide and 5.35 g (50 mmol) of dimethyloxophosphorylmethylamine are stirred together with 250 mg of silver oxide in 20 ml of acetonitrile at RT for 24 hours. After the solvent has evaporated off, the crude product is purified by chromatography over silica gel (methylene chloride/methanol: 8/1).
Yield: 2.4 g of oil MS: 299 (M+H)$^\oplus$ Example 76d

| |
|---|
| $R^5$ = OCOCH$_2$—N—(CH$_2$PO(CH$_3$)$_2$]—CH$_2$CH$_2$—N(CH$_3$)-Z {[N-benzyloxycarbonyl-N-methyl-N-(2-dimethyl-oxophosphorylmethyl)-amino-ethyl]amino}-acetyloxy |
| $R^{5*}$ = OH |
| W = F.15 |

250.4 mg (0.2 mmol) of the compound from Example 1, (0.4 mmol) 119.3 mg of the compound from Example 76c and a catalytic amount of 10 mg of potassium iodide are dissolved together in 2 ml of acetonitrile and the solution is stirred at RT for 12 hours. After the solvent has evaporated off, the crude product is purified by chromatography over silica gel. (Methylene chloride/methanol: 15/1)
MS: 1470.5 (M+H)$^\oplus$ Example 77

| |
|---|
| $R^5$ = OCOCH$_2$—N—(CH$_2$PO(CH$_3$)$_2$]—CH$_2$CH$_2$—N(CH$_3$)—H {[N-methyl-N-(2-dimethyloxophosphorylmethyl)-aminoethyl]amino}-acetyloxy |
| $R^{5*}$ = $R^5$ |
| W = F.15 |

350 g of the product from Example 77d are dissolved in 10 ml of glacial acetic acid/methanol: 2/1 and hydrogenated with 80 mg of catalyst (10% of Pd/C) at RT for 40 minutes. The catalyst is filtered off and the filtrate is evaporated to dryness in vacuo. 260 mg of the title compound remain. MS: 1541 (M+H)$^\oplus$ Example 77a

| |
|---|
| $R^5$ = OCOCH$_2$—N—(CH$_2$PO(CH$_3$)$_2$]—CH$_2$CH$_2$—N(CH$_3$)-Z {[N-benzyloxycarbonyl-N-methyl-N-(2-dimethyl-oxophosphorylmethyl)-amino-ethyl]amino}-acetyloxy |
| $R^{5*}$ = $R^5$ |
| W = F.15 |

The synthesis is carried out by a method analogous to that described in Example 46a or 76d from 76c and the compound from Example 2.

MS: 1808 (M+H)$^\oplus$

Example 78

| |
|---|
| $R^5$ = OCO—CH$_2$—N(CH$_3$)—CH$_2$CH$_2$—NH—CH$_2$PO(CH$_3$)$_2$ {N-methyl-N-[-(2-dimethyloxophosphorylmethyl)-aminoethyl]amino}-acetyloxy |
| $R^{5*}$ = OH |
| W = F.15 |

The protective groups are split off from 78c by a method analogous to that described in Example 45.
MS: 1336 (M+H)$^\oplus$ Example 78a
Z—(CH$_3$)N—CH$_2$CH$_2$—N(Boc)—CH$_2$PO(CH$_3$)$_2$ N-tert-butyloxycarbonyl-[N-dimethyloxophosphorylmethyl-(N-benzyloxycarbonyl-2-methyl-aminoethyl)]amine 1.49 g (5 mmol) of N-dimethyloxophosphorylmethyl-(N-benzyloxycarbonyl-2-methyl-aminoethyl)amine 76c and 1.13 g (5.2 mmol) of di-tert-butyl dicarbonate are dissolved together in 5 ml of acetonitrile and the solution is stirred at RT for 4 hours. It is then concentrated under a rotary evaporator in vacuo, the residue is taken up in ethyl acetate and the mixture is washed several times with 10% strength citric acid solution and saturated sodium chloride solution. It is dried with Na$_2$SO$_4$ and filtered and the filtrate is concentrated to dryness on a rotary evaporator in vacuo.
Yield: 1.7 g of oil MS: 399 (M+H)$^\oplus$ Example 78b
H—(CH$_3$)N—CH$_2$CH$_2$—N(Boc)—CH$_2$PO(CH$_3$)$_2$ N-tert-butyloxycarbonyl-[N-dimethyloxophosphorylmethyl-(N-2-methylaminoethyl)]amine 1.5 g of N-tert-butyloxycarbonyl-[N-dimethyloxophosphorylmethyl (N-benzyloxycarbonyl-2-methylaminoethyl)]-amine are hydrogenated in 20 ml of methanol with 150 mg of catalyst (10% of Pd/charcoal) at RT for 4 hours. The catalyst is filtered off and the filtrate is evaporated to dryness in vacuo.
Yield: 0.99 g of oil MS: 265 (M+H)$^\oplus$ Example 78c
$R^5$=OCO—CH$_2$—N(CH$_3$)—CH$_2$CH$_2$—N(Boc)—CH$_2$PO(CH$_3$)$_2$
$R^{5*}$=OH The synthesis is carried out by a method analogous to that described in Example 45g from 78b and the compound from Example 1. MS: 1436 (M+H)$^\oplus$ Example 79

| |
|---|
| $R^5$ = OCO—CH$_2$—N(CH$_3$)CH$_2$CH$_2$—NH—CH$_2$PO(CH$_3$)$_2$ {N-methyl-N-[-(2-dimethyloxophosphorylmethyl)-aminoethyl]amino}-acetyloxy |
| $R^{5*}$ = $R^5$ |
| W = F.15 |

The protective groups are split off from 79a by a method analogous to that described in Example 45.
MS: 1541 (M+H)$^\oplus$ Example 79a
$R^5$=OCO—CH$_2$—N(CH$_3$)—CH$_2$CH$_2$—NH—CH$_2$PO(CH$_3$)$_2${N-methyl-n-[2-N-tert-butyloxycarbonyl-(2-dimethyloxo-phosphorylmethyl)aminoethyl]amino}-acetyloxy

57

$R^{5*}=R^5$
W=F.15
The synthesis is carried out by a method analogous to that described in Example 46a from 78b and the compound from Example 2.
MS: 1740 (M+H)$^\oplus$ Example 80

$R^5$=OCOCH$_2$—N—[CH$_2$CO$_2$H ]—CH$_2$CH$_2$—N(CH$_3$)—H
$R^{5*}$=OH
W=F.15

The protective groups are split off from 80c by a method analogous to that described in Example 45h.

Example 80a

Z—(CH$_3$)N—CH$_2$CH$_2$—NH—CH$_2$COOCH(CH$_3$)$_3$ N-tert-butyloxycarbonylmethyl-(N-benzyloxycarbonyl-2-methylaminoethyl)amine 6.5 g (50 mmol) of glycine tert-butyl ester, 2.7 g (10 mmol) of (N-benzyloxycarbonyl-2-methylaminoethyl) bromide [76b] and 100 mg of silver oxide are stirred in 20 ml of acetonitrile at RT for 24 hours. The reaction solution is filtered and the filtrate is evaporated in vacuo. The residue is taken up in ethyl acetate and the mixture is washed several times with water and saturated NaCl solution to remove H-Gly-OBut. The ethyl acetate solution is dried with Na$_2$SO$_4$, filtered and evaporated in vacuo. The crude product is purified by chromatography over silica gel. (Methylene chloride/methanol: 30/1)
Yield: 2.7 g of oil MS: 323 (M+H)$^\oplus$ Example 80b

| | |
|---|---|
| $R^5$ = | OCOCH$_2$—N—[CH$_2$CO$_2^t$Bu]—CH$_2$CH$_2$—N(CH$_3$)-Z {[N-benzyloxycarbonyl-N-methyl-N(tert-butyloxy-carbonylmethyl)amino-ethyl]amino}-acetyloxy |
| $R^{5*}$ = | OH |
| W = | F.15 |

The synthesis is carried out by a method analogous to that described in Example 45g from 80a and the compound from Example 1. MS: 1495 (M+H)$^\oplus$ Example 80c

| | |
|---|---|
| $R^5$ = | OCOCH$_2$—N—[CH$_2$CO$_2^t$Bu]—CH$_2$CH$_2$—N(CH$_3$)—H {[N-methyl-N(tert-butyloxycarbonylmethyl)amino-ethyl]amino}-acetyloxy |
| $R^{5*}$ = | OH |
| W = | F.15 |

550 mg of the compound 80b were dissolved in 10 ml of methanol and hydrogenated with 100 mg of catalyst (10% of Pd/C) at RT for 2 hours. The catalyst was removed by filtration and the filtrate was evaporated to dryness in vacuo. The residue was triturated with diethyl ether, filtered off with suction, washed and dried in a desiccator.
Yield: 411 mg of the diacetate MS: 1361 (M+H)$^\oplus$ Example 81

$R^5$ s OCOCH$_2$—N—[CH$_2$CO$_2^t$Bu]—CH$_2$CH$_2$—N(CH$_3$)—H
$R^{5*}$=$R^5$
W=F.15

200 mg of 81a were dissolved in 10 ml of methanol/ glacial acetic acid (1/1) and hydrogenated with 20 mg of catalyst (10% of Pd/C) at RT for 1 hour. After removal of the catalyst and the solvent, the residue was triturated with diethyl ether, filtered off with suction, washed and dried in a desiccator.
Yield: 140 mg of the tetra acetate MS: 1588.8 (M+H)$^\oplus$ Example 81a $R^5$=OCOCH$_2$—N—[CH$_2$CO$_2^t$Bu]—CH$_2$CH$_2$—N(CH$_3$)—Z
$R^{5*}$=$R^5$
W=F.15

The synthesis is carried out by a method analogous to that described in Example 46a from 80a and the compound from Example 2. MS: 1857.2 (M+H)$^\oplus$ Example 82

| | |
|---|---|
| $R^5$ = | OCOCH$_2$—N(CH$_3$)—CH$_2$CH$_2$—N(Boc)CH$_2$COOCH(CH$_3$)$_3$ {N-methyl-N-[2-N-tert-butyloxycarbonyl-(2-tert-butyloxycarbonylmethyl)amino-ethyl]amino}-acetyloxy |
| $R^{5*}$ = | OH |
| W = | F.15 |

The synthesis is carried out by a method analogous to that described in Example 45g from 82b and the compound from Example 1.
MS: 1459.7 (M+H)$^\oplus$ Example 82a Z—N(CH$_3$)—CH$_2$CH$_2$—N(Boc)—CH$_2$COOCH(CH$_3$)$_3$ N-tert-butyloxycarbonyl-[N-tert-butyloxycarbonylmethyl-(N-benzyloxycarbonyl-2-methyl-amino-ethyl)]amine 2.25 g (7 mmol) of N-tert-butyloxycarbonylmethyl-(N-benzyloxycarbonyl-2-methylaminoethyl)amine [80a] and 2.32 g (7.2 mmol) of di-tert-butyldicarbonate are stirred together in 10 ml of acetonitrile at RT for 4 hours. The mixture is then concentrated on a rotary evaporator and the residue is purified by chromatography over silica gel. (Methylene chloride/methanol: 60/1)
Yield: 2.2 g of oil MS: 423 (M+H)$^\oplus$ Example 82b H—(CH$_3$)N—CH$_2$CH$_2$—N(Boc)—CH$_2$COOCH(CH$_3$)$_3$ N-tert-butyloxycarbonyl-[N-tert-butyloxycarbonylmethyl-(2-methylaminoethyl)amine 2 g of N-tert-butyloxycarbonyl-N-(tert-butyloxycarbonyl-methyl-(N-benzyloxycarbonyl-2-methyl-aminoethyl)amine are dissolved in 20 ml of methanol and hydrogenated with 100 mg of catalyst (10% of Pd/C) at RT for 4 hours. The catalyst is filtered off and the filtrate is evaporated to dryness.
Yield: 1.4 g of oil MS: 289 (M+H)$^\oplus$ Example 83

| | |
|---|---|
| $R^5$ = | OCOCH$_2$—N(CH$_3$)—CH$_2$CH$_2$—N(Boc)-CH$_2$COOCH(CH$_3$)$_3$ {N-methyl-N-[2-N-tert-butyloxycarbonyl-(2-tert-butyloxycarbonylmethyl)-amino-ethyl]-amino}-acetyloxy |
| $R^{5*}$ = | $R^5$ |
| W = | F.15 |

The synthesis is carried out by a method analogous to that described in Example 46a from 82b and the compound from Example 2.

MS: 1789 (M+H)⊕

Figure 2A:
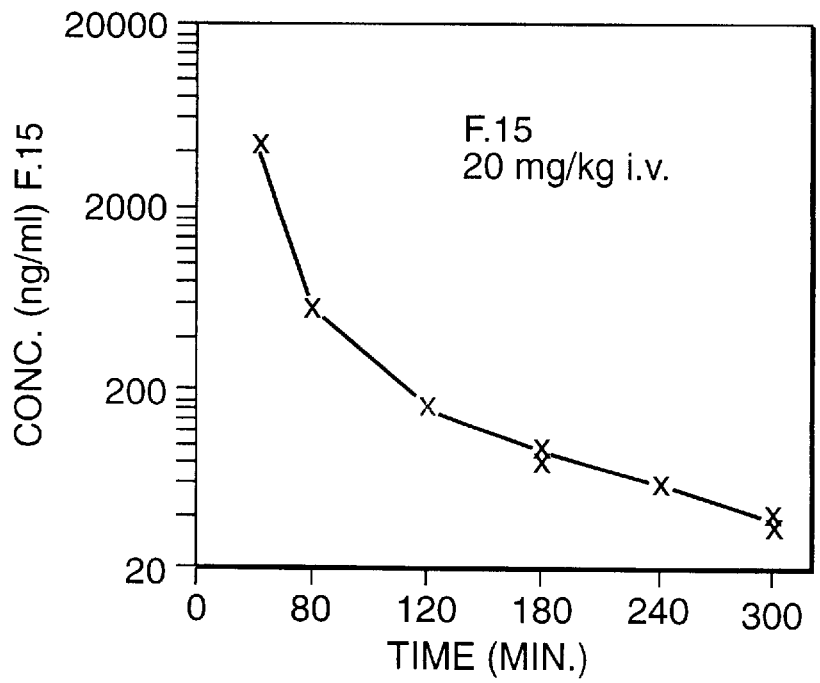
FIG. 2A shows the serum concentration of the active compound F.15 plotted against time following intravenous administration of F.15 to NMRI mice.
Figure 2B:
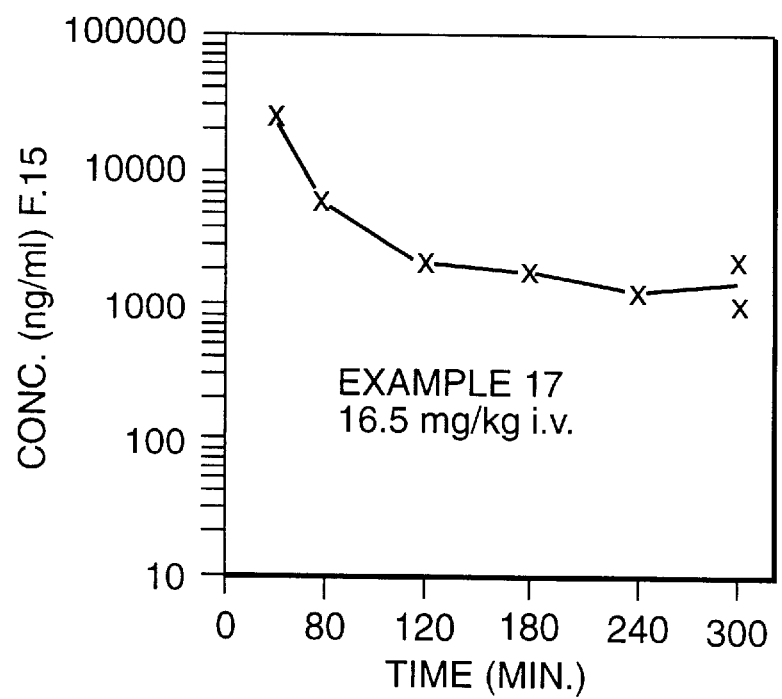
FIG. 2B shows the serum concentration of the active compound F.15 plotted against time following intravenous administration of F.15 and the compound described in Example 17 to NMRI mice.

Example 84
Determination of the pharmaco kinetic properties of the compounds of the formula I The preparations were administered subcutaneously, intravenously or orally by means of a stomach tube to NMRI mice. At certain points in time, a cardiac puncture was performed under anesthetic on in each case 2 or 3 mice. The anesthesia is achieved by intraperitoneal administration of 0.3 ml of a urethane solution (0.2 mg/ml). The blood withdrawn was stored at 4° C. until coagulated and then centrifuged. The serum thus obtained was centrifuged again for purification (Eppendorff centrifuge model 5414.5 minutes). The serum was stored at −20° C. until analyzed. The samples were analyzed by ether extraction and subsequent separation by means of RP-HPLC. The results were plotted on a graph. In FIG. 1 (s.c. administration) and in FIG. 2 (i.v. administration), the serum concentration of the active compound F.15 is plotted against the time after the administration of the active compound F.15 and after the administration of various compounds from the examples described above. In addition to the improved water-solubility of the prodrug compounds, improved pharmacokinetics can also be detected.

We claim:

1. An ester compound comprising the mono or bis-dehydroxylated radical of a compound of the formula:

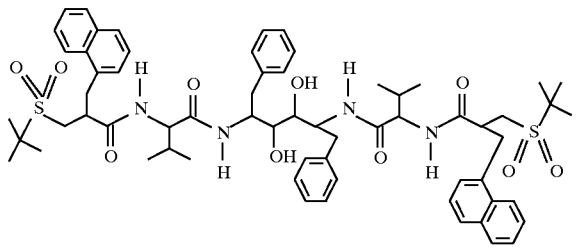

wherein the radical is substituted, at the point or points of dehydroxylation, with a radical of the formula $R^5$, wherein $R^5$ is a radical of the formula III, IV, or V:

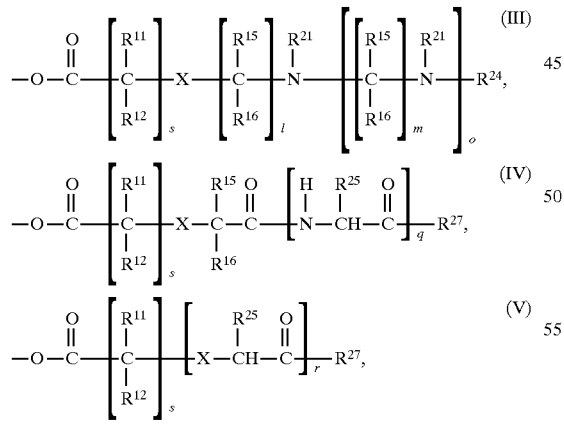

wherein

X is O, S, $NR^{20}$ or $N^+(R^{20})_2$, $R^{20}$ is H, $(C_1-C_6)$-alkyl, $(C_3-C_7)$-cycloalkyl, $-CH_2-(CH_2)_n-NR^{21}R^{24}$, $-CH_2-C(O)-R^{28}$, $CH_2CONH(C_1-C_6)$-alkyl, which can be substituted by up to 5 OH groups, $COO(C_1-C_6)$-alkyl or $-CH_2-P(O)((C_1-C_4)$-alkyl)$_2$, $R^{11}$, $R^{12}$, $R^{15}$ and $R^{16}$ independently of one another are H or $(C_1-C_4)$-alkyl, $R^{21}$ is H, $(C_1-C_6)$-alkyl, $(C_3-C_7)$-cycloalkyl or $(C_1-C_4)$-alkyloxycarbonyl, $R^{24}$ is H, $(C_1-C_{18})$-alkyl, $(C_3-C_{14})$-cycloalkyl, $(C_2-C_{18})$-alkenyl, $(C_2-C_{18})$-alkynyl or $(C_6-C_{14})$-aryl, each of which can be mono-, di- or trisubstituted by $(C_6-C_{14})$-aryl, $(C_6-C_{14})$-aryloxy, $(C_3-C_{14})$-cycloalkyl, hydroxyl, $(C_1-C_4)$-alkoxy, $-C(O)-R^{28}$, $P(O)((C_1-C_4)$-alkyl)$_2$, $NH_2$ or halogen and are linked with $NR^{21}$ directly or optionally via CO, or an α-amino acid linked via the carbonyl group, or $R^{24}$ is $((C_1-C_4)$-alkyl)$-N((C_1-C_4)$-alkyl)$-(C_1-C_4)$-alkyl-NH$-((C_1-C_4)$-alkyl), or $R^{24}$ forms a heterocyclic radical with $R^{21}$, and $R^{25}$ is a side chain of an amino acid, $R^{27}$ and $R^{28}$ independently of one another are OH, $O-(C^1-C_6)$-alkyl, $O-(C_3-C_6)$-cycloalkyl $NH_2$, $NH-(C_1-C_6)$-alkyl, which can be substituted by up to 5 OH groups, $-NH-(C_3-C_7)$-cycloalkyl or $-N$-bis$(C_1-C_4)$-alkyl, l can be 2 or 3, s can be 1, 2, 3, 4 or 5, m can be 0, 1, 2, 3 or 4, n can be 1, 2 or 3, o can be 0, 1, 2 or 3, q can be 0, 1, 2 or 3, and r can be 1, 2 or 3.

2. The compound as claimed in claim 1, wherein $R^5$ is a radical of the formula III or IV, X is S or $NR^{20}$, $R^{20}$ is H, $(C_1-C_4)$-alkyl, $-CH_2-C(O)-R^{28}$ or $-CH_2-P(O)Me_2$, $R^{11}$, $R^{12}$, $R^{15}$ and $R^{16}$ independently of one another are H or methyl, $R^{21}$ is H or $(C_1-C_4)$-alkyl, $R^{24}$ is H, $(C_1-C_4)$-alkyl, which can optionally be substituted by phenyl, $NH_2$ or $(C_3-C_7)$-cycloalkyl and is linked with $NR^{21}$ directly or optionally via CO, a naturally occurring α-amino acid linked via the carbonyl group, $-CH_2C(O)R^{28}$, $-CH_2-P(O)Me_2$ or $-(CH_2)_3N(Me)(CH_2)_2NHMe$, $R^{25}$ is a side chain of Asp, Glu, Lys, Arg or Orn, $R^{27}$ and $R^{28}$ are independently of one another OH, $NH_2$, $O(C_1-C_4)$-alkyl, $-NH-(C_1-C_4)$-alkyl or $-N$-bis$(C_1-C_4)$-alkyl, l is 2, s can be 1, 4 or 5, m can be 2 or 3, n can be 1 or 2, o can be 0, 1 or 2, q can be 1 or 2, and r can be 1 or 2.

3. The compound of claim 2, wherein $R^{20}$ is H or $(C_1-C_4)$-alkyl, $R^{24}$ is H or $(C_1-C_4)$-alkyl, $R^{27}$ and $R^{28}$ independently of one another are OH, $NH_2$ or $O(C_1-C_4)$-alkyl, s is 1, o is 0, q is 1, and r is 1 or 2.

4. A process for the preparation of the compound claimed in claim 1, comprising:

reacting an active compound of the formula:

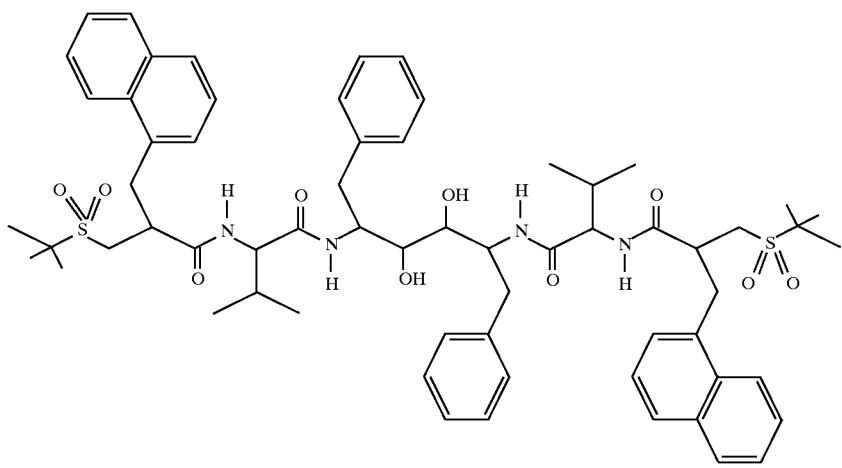

with a compound of the formula (X):

;and reacting the resulting compound of the formula (XX) with a nucleophile of the formulae (XI), (XII), or (XIII)

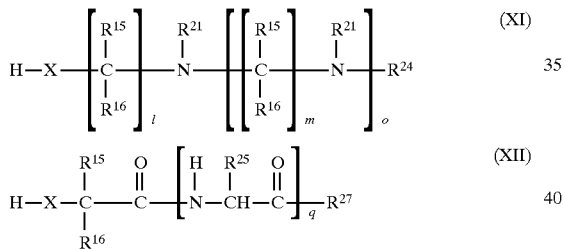

-continued

in which X, $R^{11}$, $R^{12}$, $R^{15}$, $R^{16}$, $R^{21}$, $R^{24}$, $R^{25}$, $R^{27}$, l, m, n, o, q, r and s have the meanings set forth in claim 1, V is a suitable leaving group, and AG is a leaving group which is suitable for esterification or a group that results from active ester methods for carboxylic acids.

5. The process of claim 4, wherein V is Br, Cl or OTs, and AG is Br or Cl, or a group that results from active ester methods for carboxylic acids.

6. A pharmaceutical composition comprising a compound as claimed in claim 1 together with a pharmaceutically acceptable carrier.

* * * * *